(12) United States Patent
Clark et al.

(10) Patent No.: US 8,808,345 B2
(45) Date of Patent: Aug. 19, 2014

(54) HANDLE ASSEMBLIES FOR INTRAVASCULAR TREATMENT DEVICES AND ASSOCIATED SYSTEMS AND METHODS

(75) Inventors: Benjamin J. Clark, Redwood City, CA (US); William R. George, Santa Cruz, CA (US); Kenneth J. Michlitsch, Livermore, CA (US); John Paul Sam, Los Altos, CA (US); Erik Thai, San Jose, CA (US); Andrew Wu, Foster City, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 345 days.

(21) Appl. No.: 12/759,641

(22) Filed: Apr. 13, 2010

(65) Prior Publication Data

US 2010/0249773 A1    Sep. 30, 2010

Related U.S. Application Data

(63) Continuation-in-part of application No. PCT/US2009/069334, filed on Dec. 22, 2009, and a (Continued)

(30) Foreign Application Priority Data

Aug. 14, 2009  (EP) .................................... 09167937
Aug. 14, 2009  (EP) .................................... 09168202
Aug. 14, 2009  (EP) .................................... 09168204

(51) Int. Cl.
*A61B 18/08* (2006.01)
*A61B 19/00* (2006.01)
*A61B 17/00* (2006.01)
*A61B 18/00* (2006.01)

(52) U.S. Cl.
CPC ......... *A61B 18/08* (2013.01); *A61B 2019/2269* (2013.01); *A61B 2017/003* (2013.01); *A61B 2018/00916* (2013.01)
USPC .......................................... 607/113; 604/528

(58) Field of Classification Search
CPC ............ A61B 2018/0091; A61B 2018/00952; A61B 2017/003; A61B 2017/00389
USPC .............................. 607/113; 606/41; 604/528
See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| CN | 102525646 | 7/2012 |
| EP | 0521595 A2 | 1/1993 |

(Continued)

OTHER PUBLICATIONS

U.S. Appl. No. 12/790,639, Wu et al.

(Continued)

*Primary Examiner* — Linda Dvorak
*Assistant Examiner* — Jocelyn D Ram

(57) ABSTRACT

The present disclosure comprises handle assemblies for intravascular treatment devices. In one embodiment, a handle assembly comprises an actuator for deflecting a distal region of an intravascular treatment device. In one embodiment, a handle assembly comprises a rotator for rotating an intravascular treatment device independently of the handle assembly. In one embodiment, a handle assembly comprises a rotation limiting element for limiting independent rotation of an intravascular treatment device relative to the handle assembly. Methods and systems for intravascular delivery, deflection and placement of an intravascular treatment device via a handle assembly of the present invention are also provided.

13 Claims, 15 Drawing Sheets

Related U.S. Application Data continuation-in-part of application No. 12/545,648, filed on Aug. 21, 2009, now Pat. No. 8,652,129, and a continuation-in-part of application No. 12/495,691, filed on Jun. 30, 2009.

(60) Provisional application No. 61/142,128, filed on Dec. 31, 2008.

(56) References Cited

U.S. PATENT DOCUMENTS

| | | | |
|---|---|---|---|
| 4,664,113 A * | | 5/1987 | Frisbie et al. ............... 606/194 |
| 4,764,504 A | | 8/1988 | Johnson et al. |
| 4,976,711 A | | 12/1990 | Parins et al. |
| 5,055,109 A * | | 10/1991 | Gould et al. ............... 604/95.01 |
| 5,114,403 A * | | 5/1992 | Clarke et al. ............... 604/95.04 |
| 5,185,004 A * | | 2/1993 | Lashinski ............... 604/95.04 |
| 5,195,968 A | | 3/1993 | Lundquist et al. |
| 5,199,950 A | | 4/1993 | Schmitt et al. |
| 5,217,440 A | | 6/1993 | Frassica |
| 5,242,430 A * | | 9/1993 | Arenas et al. ............... 16/110.1 |
| 5,242,441 A | | 9/1993 | Avitall |
| 5,254,088 A | | 10/1993 | Lundquist et al. |
| 5,275,151 A | | 1/1994 | Shockey et al. |
| 5,292,315 A | | 3/1994 | Euteneuer |
| 5,300,068 A | | 4/1994 | Rosar et al. |
| 5,308,324 A | | 5/1994 | Hammerslag et al. |
| 5,318,525 A | | 6/1994 | West et al. |
| 5,318,526 A | | 6/1994 | Cohen |
| 5,327,905 A | | 7/1994 | Avitall |
| 5,334,145 A | | 8/1994 | Lundquist et al. |
| 5,352,197 A * | | 10/1994 | Hammersmark et al. .... 604/528 |
| 5,354,297 A | | 10/1994 | Avitall |
| 5,358,478 A | | 10/1994 | Thompson et al. |
| 5,358,514 A | | 10/1994 | Schulman et al. |
| 5,360,406 A | | 11/1994 | Boykin et al. |
| 5,364,351 A | | 11/1994 | Heinzelman et al. |
| 5,364,352 A * | | 11/1994 | Cimino et al. ............... 604/95.04 |
| 5,365,928 A | | 11/1994 | Rhinehart et al. |
| 5,368,591 A | | 11/1994 | Lennox et al. |
| 5,368,592 A | | 11/1994 | Stern et al. |
| 5,391,147 A | | 2/1995 | Imran et al. |
| 5,395,327 A | | 3/1995 | Lundquist et al. |
| 5,395,329 A | | 3/1995 | Fleischhacker et al. |
| 5,397,304 A | | 3/1995 | Truckai |
| 5,399,164 A | | 3/1995 | Snoke et al. |
| 5,423,744 A | | 6/1995 | Gencheff et al. |
| 5,431,168 A | | 7/1995 | Webster, Jr. |
| 5,439,006 A | | 8/1995 | Brennen et al. |
| 5,441,483 A | | 8/1995 | Avitall |
| 5,445,148 A | | 8/1995 | Jaraczewski et al. |
| 5,448,989 A | | 9/1995 | Heckele |
| 5,456,664 A | | 10/1995 | Heinzelman et al. |
| 5,465,716 A * | | 11/1995 | Avitall ............... 600/374 |
| 5,482,037 A | | 1/1996 | Borghi |
| 5,484,400 A | | 1/1996 | Edwards et al. |
| 5,487,757 A | | 1/1996 | Truckai et al. |
| 5,489,270 A | | 2/1996 | van Erp |
| 5,545,200 A | | 8/1996 | West et al. |
| 5,562,619 A | | 10/1996 | Mirarchi et al. |
| 5,571,147 A | | 11/1996 | Sluijter et al. |
| 5,599,345 A | | 2/1997 | Edwards et al. |
| 5,603,697 A | | 2/1997 | Grundy et al. |
| 5,611,777 A * | | 3/1997 | Bowden et al. ............. 604/95.01 |
| 5,626,576 A | | 5/1997 | Janssen |
| 5,643,255 A | | 7/1997 | Organ |
| 5,656,029 A | | 8/1997 | Imran et al. |
| 5,672,174 A | | 9/1997 | Gough et al. |
| 5,685,878 A | | 11/1997 | Falwell et al. |
| 5,688,266 A | | 11/1997 | Edwards et al. |
| 5,700,282 A | | 12/1997 | Zabara |
| 5,707,400 A | | 1/1998 | Terry, Jr. et al. |
| 5,772,590 A | | 6/1998 | Webster, Jr. |
| 5,797,842 A | | 8/1998 | Pumares et al. |
| 5,807,249 A | | 9/1998 | Qin et al. |
| 5,823,955 A * | | 10/1998 | Kuck et al. ............... 600/374 |
| 5,827,272 A | | 10/1998 | Breining et al. |
| 5,843,076 A | | 12/1998 | Webster, Jr. et al. |
| 5,849,028 A | | 12/1998 | Chen |
| 5,855,560 A | | 1/1999 | Idaomi et al. |
| 5,860,953 A | | 1/1999 | Snoke et al. |
| 5,865,787 A | | 2/1999 | Shapland |
| 5,865,800 A | | 2/1999 | Mirarchi et al. |
| 5,873,842 A | | 2/1999 | Brennen et al. |
| 5,891,088 A | | 4/1999 | Thompson et al. |
| 5,893,885 A | | 4/1999 | Webster et al. |
| 5,897,529 A | | 4/1999 | Ponzi |
| 5,935,102 A | | 8/1999 | Bowden et al. |
| 5,935,124 A | | 8/1999 | Klumb et al. |
| 5,938,603 A | | 8/1999 | Ponzi |
| 5,944,710 A | | 8/1999 | Dev et al. |
| 5,951,471 A | | 9/1999 | de la Rama et al. |
| 5,954,719 A | | 9/1999 | Chen et al. |
| 5,983,141 A | | 11/1999 | Sluijter et al. |
| 5,987,344 A | | 11/1999 | West |
| 6,004,269 A | | 12/1999 | Crowley et al. |
| 6,009,877 A | | 1/2000 | Edwards |
| 6,027,460 A | | 2/2000 | Shturman |
| 6,027,473 A | | 2/2000 | Ponzi |
| 6,066,134 A | | 5/2000 | Eggers et al. |
| 6,096,036 A | | 8/2000 | Bowe et al. |
| 6,099,524 A | | 8/2000 | Lipson et al. |
| 6,117,101 A | | 9/2000 | Diederich et al. |
| 6,120,476 A | | 9/2000 | Fung et al. |
| 6,135,999 A | | 10/2000 | Fanton et al. |
| 6,146,355 A | | 11/2000 | Biggs |
| 6,149,620 A | | 11/2000 | Baker et al. |
| 6,161,048 A | | 12/2000 | Sluijter et al. |
| 6,171,277 B1 | | 1/2001 | Ponzi |
| 6,179,809 B1 | | 1/2001 | Khairkhahan et al. |
| 6,183,463 B1 | | 2/2001 | Webster, Jr. |
| 6,198,974 B1 | | 3/2001 | Webster, Jr. |
| 6,203,525 B1 | | 3/2001 | Whayne et al. |
| 6,210,362 B1 | | 4/2001 | Ponzi |
| 6,210,407 B1 | | 4/2001 | Webster |
| 6,219,577 B1 | | 4/2001 | Brown, III et al. |
| 6,224,587 B1 | | 5/2001 | Gibson |
| 6,224,592 B1 | | 5/2001 | Eggers et al. |
| 6,246,912 B1 | | 6/2001 | Sluijter et al. |
| 6,246,914 B1 | | 6/2001 | de la Rama et al. |
| 6,254,568 B1 | | 7/2001 | Ponzi |
| 6,263,224 B1 | | 7/2001 | West |
| 6,270,476 B1 | | 8/2001 | Santoianni et al. |
| 6,273,886 B1 | | 8/2001 | Edwards et al. |
| 6,280,423 B1 | | 8/2001 | Davey et al. |
| 6,283,951 B1 | | 9/2001 | Flaherty et al. |
| 6,292,695 B1 | | 9/2001 | Webster, Jr. et al. |
| 6,314,325 B1 | | 11/2001 | Fitz |
| 6,322,558 B1 | | 11/2001 | Taylor et al. |
| 6,322,559 B1 | | 11/2001 | Daulton et al. |
| 6,356,790 B1 | | 3/2002 | Maguire et al. |
| 6,394,976 B1 | | 5/2002 | Winston et al. |
| 6,405,732 B1 | | 6/2002 | Edwards et al. |
| 6,413,255 B1 | | 7/2002 | Stern |
| 6,468,260 B1 | | 10/2002 | Bumbalough et al. |
| 6,488,679 B1 | | 12/2002 | Swanson et al. |
| 6,500,167 B1 | | 12/2002 | Webster, Jr. |
| 6,506,189 B1 | | 1/2003 | Rittman, III et al. |
| 6,511,471 B2 | | 1/2003 | Rosenman et al. |
| 6,514,226 B1 | | 2/2003 | Levin et al. |
| 6,522,926 B1 | | 2/2003 | Kieval et al. |
| 6,530,897 B2 | | 3/2003 | Nardeo |
| 6,544,215 B1 | | 4/2003 | Bencini et al. |
| 6,551,271 B2 | | 4/2003 | Nguyen |
| 6,551,302 B1 | | 4/2003 | Rosinko et al. |
| 6,562,034 B2 | | 5/2003 | Edwards et al. |
| 6,569,114 B2 | | 5/2003 | Ponzi et al. |
| 6,602,242 B1 | | 8/2003 | Fung et al. |
| 6,602,278 B1 | | 8/2003 | Thompson et al. |
| 6,616,624 B1 | | 9/2003 | Kieval |
| 6,616,628 B2 | | 9/2003 | Hayzelden |
| 6,622,731 B2 | | 9/2003 | Daniel et al. |
| 6,635,054 B2 | | 10/2003 | Fjield et al. |
| 6,685,648 B2 | | 2/2004 | Flaherty et al. |

(56) References Cited

U.S. PATENT DOCUMENTS

| | | |
|---|---|---|
| 6,736,835 B2 | 5/2004 | Pellegrino et al. |
| 6,776,765 B2 | 8/2004 | Soukup et al. |
| 6,783,510 B1 | 8/2004 | Gibson et al. |
| 6,783,521 B2 | 8/2004 | Ponzi et al. |
| 6,837,867 B2 | 1/2005 | Kortelling |
| 6,845,267 B2 | 1/2005 | Harrison et al. |
| 6,850,801 B2 | 2/2005 | Kieval et al. |
| 6,885,888 B2 | 4/2005 | Rezai |
| 6,893,436 B2 | 5/2005 | Woodard et al. |
| 6,926,711 B2 | 8/2005 | Lentz et al. |
| 6,939,346 B2 | 9/2005 | Kannenberg et al. |
| 6,978,174 B2 | 12/2005 | Gelfand et al. |
| 6,979,319 B2 | 12/2005 | Manning et al. |
| 6,987,995 B2 | 1/2006 | Drysen |
| 7,008,401 B2 | 3/2006 | Thompson et al. |
| 7,056,314 B1 | 6/2006 | Florio et al. |
| 7,063,682 B1 | 6/2006 | Whayne et al. |
| 7,077,823 B2 | 7/2006 | McDaniel |
| 7,101,361 B2 | 9/2006 | Gardeski |
| 7,122,020 B2 | 10/2006 | Mogul |
| 7,149,574 B2 | 12/2006 | Yun et al. |
| 7,162,303 B2 | 1/2007 | Levin et al. |
| 7,221,979 B2 | 5/2007 | Zhou et al. |
| 7,232,422 B2 | 6/2007 | Gibson et al. |
| 7,274,957 B2 | 9/2007 | Drysen |
| 7,285,108 B2 | 10/2007 | Koerner et al. |
| 7,300,438 B2 | 11/2007 | Falwell et al. |
| 7,374,553 B2 | 5/2008 | Koerner et al. |
| 7,377,906 B2 | 5/2008 | Selkee |
| 7,381,200 B2 | 6/2008 | Katoh et al. |
| 7,390,894 B2 | 6/2008 | Weinshilboum et al. |
| 7,402,151 B2 | 7/2008 | Rosenman et al. |
| 7,465,288 B2 | 12/2008 | Dudney et al. |
| 7,503,914 B2 | 3/2009 | Coleman et al. |
| 7,588,555 B2 | 9/2009 | Pudelko et al. |
| 7,591,784 B2 | 9/2009 | Butler |
| 7,591,799 B2 | 9/2009 | Selkee |
| 7,615,044 B2 | 11/2009 | Scheibe et al. |
| 7,617,005 B2 | 11/2009 | Demarais et al. |
| 7,618,413 B2 | 11/2009 | Weitzner et al. |
| 7,620,451 B2 | 11/2009 | Demarais et al. |
| 7,632,265 B2 | 12/2009 | Hauck et al. |
| 7,647,115 B2 | 1/2010 | Levin et al. |
| 7,653,438 B2 | 1/2010 | Deem et al. |
| 7,678,074 B2 | 3/2010 | Fischer |
| 7,678,104 B2 | 3/2010 | Keidar |
| 7,682,358 B2 | 3/2010 | Gullickson et al. |
| 7,691,095 B2 | 4/2010 | Bednarek et al. |
| 7,706,894 B2 | 4/2010 | Stewart et al. |
| 7,717,948 B2 | 5/2010 | Demarais et al. |
| 7,720,517 B2 | 5/2010 | Drysen |
| 7,756,583 B2 | 7/2010 | Demarais et al. |
| 7,771,388 B2 | 8/2010 | Olsen et al. |
| 7,778,703 B2 | 8/2010 | Gross et al. |
| 7,780,648 B2 | 8/2010 | McIntyre et al. |
| 7,803,130 B2 | 9/2010 | Ryan et al. |
| 7,811,277 B2 | 10/2010 | Boulais |
| 7,819,857 B2 | 10/2010 | Ponzi et al. |
| 7,828,791 B2 | 11/2010 | Long et al. |
| 7,842,025 B2 | 11/2010 | Coleman et al. |
| 7,853,302 B2 | 12/2010 | Rodriguez et al. |
| 7,879,004 B2 | 2/2011 | Seibel et al. |
| 7,881,809 B2 | 2/2011 | Rashidi |
| 7,892,186 B2 | 2/2011 | Soukup et al. |
| 7,909,821 B2 | 3/2011 | Paddock et al. |
| 7,917,187 B2 | 3/2011 | Fuimaono et al. |
| 7,931,616 B2 | 4/2011 | Selkee |
| 7,955,314 B2 | 6/2011 | Fischer et al. |
| 7,959,601 B2 | 6/2011 | McDaniel et al. |
| 8,002,739 B2 | 8/2011 | Lee et al. |
| 8,007,462 B2 | 8/2011 | Gibson et al. |
| 8,007,463 B2 | 8/2011 | Pudelko et al. |
| 8,021,327 B2 | 9/2011 | Selkee |
| 8,043,288 B2 | 10/2011 | Dando et al. |
| 8,048,024 B2 | 11/2011 | Tah et al. |
| 8,048,025 B2 | 11/2011 | Barenboym et al. |
| 8,048,026 B2 | 11/2011 | Fischer et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,146,603 B2 * | 4/2012 | Thapliyal et al. ............. 128/898 |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0058910 A1 | 5/2002 | Hermann et al. |
| 2002/0165532 A1 | 11/2002 | Hill et al. |
| 2002/0183682 A1 | 12/2002 | Darvish |
| 2003/0040735 A1 | 2/2003 | Kunis et al. |
| 2003/0050681 A1 | 3/2003 | Pianca et al. |
| 2003/0060858 A1 | 3/2003 | Kieval et al. |
| 2003/0114832 A1 | 6/2003 | Kohler et al. |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0208219 A1 | 11/2003 | Aznoian et al. |
| 2003/0216792 A1 | 11/2003 | Levin et al. |
| 2004/0010289 A1 | 1/2004 | Biggs et al. |
| 2004/0106897 A1 | 6/2004 | Thompson et al. |
| 2004/0116897 A1 | 6/2004 | Aboul-Hosn |
| 2004/0143197 A1 | 7/2004 | Soukup et al. |
| 2004/0215139 A1 | 10/2004 | Cohen |
| 2004/0215186 A1 | 10/2004 | Cornelius et al. |
| 2005/0004515 A1 | 1/2005 | Hart et al. |
| 2005/0004644 A1 * | 1/2005 | Kelsch et al. .................. 607/131 |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0234523 A1 | 10/2005 | Levin et al. |
| 2005/0245862 A1 | 11/2005 | Seward et al. |
| 2005/0256452 A1 | 11/2005 | DeMarchi et al. |
| 2006/0025821 A1 | 2/2006 | Gelfand et al. |
| 2006/0041277 A1 | 2/2006 | Deem et al. |
| 2006/0047245 A1 | 3/2006 | Sehra |
| 2006/0095029 A1 | 5/2006 | Young et al. |
| 2006/0142695 A1 | 6/2006 | Knudson |
| 2006/0200047 A1 | 9/2006 | Galdonik et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224111 A1 | 10/2006 | Rosenman et al. |
| 2006/0235474 A1 | 10/2006 | Demarais |
| 2006/0264820 A1 | 11/2006 | Ponzi et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0156114 A1 | 7/2007 | Worley et al. |
| 2007/0156133 A1 | 7/2007 | McDaniel et al. |
| 2007/0173757 A1 | 7/2007 | Levine et al. |
| 2007/0173899 A1 | 7/2007 | Levin et al. |
| 2007/0213687 A1 | 9/2007 | Barlow |
| 2007/0225701 A1 | 9/2007 | O'Sullivan |
| 2007/0260225 A1 | 11/2007 | Sakakine et al. |
| 2007/0265609 A1 * | 11/2007 | Thapliyal et al. ............... 606/27 |
| 2007/0265687 A1 | 11/2007 | Deem et al. |
| 2008/0051703 A1 | 2/2008 | Thornton et al. |
| 2008/0154190 A1 | 6/2008 | St. Germain et al. |
| 2008/0188800 A1 | 8/2008 | Bencini et al. |
| 2008/0188869 A1 | 8/2008 | Weitzner et al. |
| 2008/0213331 A1 | 9/2008 | Gelfand et al. |
| 2008/0255540 A1 | 10/2008 | Selkee |
| 2008/0255642 A1 | 10/2008 | Zarins et al. |
| 2008/0287862 A1 | 11/2008 | Weitzner et al. |
| 2008/0319314 A1 | 12/2008 | Hill et al. |
| 2008/0319513 A1 | 12/2008 | Pu et al. |
| 2009/0036948 A1 | 2/2009 | Levin et al. |

(56) References Cited

U.S. PATENT DOCUMENTS

| | | | |
|---|---|---|---|
| 2009/0062873 A1 | 3/2009 | Wu et al. |
| 2009/0076409 A1 | 3/2009 | Wu et al. |
| 2009/0125001 A1 | 5/2009 | Anderson et al. |
| 2009/0171274 A1 | 7/2009 | Harlev et al. |
| 2009/0281524 A1 | 11/2009 | Scheibe et al. |
| 2009/0287188 A1 | 11/2009 | Golden et al. |
| 2009/0312698 A1 | 12/2009 | Farrell et al. |
| 2009/0326450 A1* | 12/2009 | Ostrovsky et al. ......... 604/95.04 |
| 2010/0004592 A1 | 1/2010 | Butler |
| 2010/0004633 A1 | 1/2010 | Rothe et al. |
| 2010/0010567 A1 | 1/2010 | Deem et al. |
| 2010/0022948 A1 | 1/2010 | Wilson et al. |
| 2010/0057150 A1 | 3/2010 | Demarais et al. |
| 2010/0063441 A1 | 3/2010 | Grunewald et al. |
| 2010/0069834 A1 | 3/2010 | Schultz |
| 2010/0087780 A1 | 4/2010 | Tekulve et al. |
| 2010/0106141 A1 | 4/2010 | Osypka et al. |
| 2010/0137860 A1 | 6/2010 | Demarais et al. |
| 2010/0137952 A1 | 6/2010 | Demarais et al. |
| 2010/0137955 A1 | 6/2010 | Milijasevic et al. |
| 2010/0152582 A1 | 6/2010 | Thapliyal et al. |
| 2010/0168731 A1 | 7/2010 | Wu et al. |
| 2010/0168739 A1 | 7/2010 | Wu et al. |
| 2010/0168740 A1 | 7/2010 | Stewart et al. |
| 2010/0174282 A1 | 7/2010 | Demarais et al. |
| 2010/0179512 A1 | 7/2010 | Chong et al. |
| 2010/0191112 A1 | 7/2010 | Demarais et al. |
| 2010/0198040 A1* | 8/2010 | Friedman et al. ............. 600/374 |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2010/0312178 A1 | 12/2010 | Olsen et al. |
| 2010/0324538 A1 | 12/2010 | Van Orden |
| 2011/0021900 A1 | 1/2011 | Ponzi et al. |
| 2011/0054287 A1 | 3/2011 | Schultz |
| 2011/0054446 A1 | 3/2011 | Schultz |
| 2011/0054465 A1 | 3/2011 | Werneth et al. |
| 2011/0077498 A1 | 3/2011 | McDaniel |
| 2011/0077621 A1 | 3/2011 | Graham et al. |
| 2011/0184385 A1 | 7/2011 | Datta et al. |
| 2011/0196346 A1 | 8/2011 | Fischer et al. |
| 2012/0043088 A1 | 2/2012 | McAllister et al. |
| 2012/0059286 A1 | 3/2012 | Hastings et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | |
|---|---|---|
| EP | 1326550 | 7/2003 |
| EP | 1968679 | 9/2008 |
| EP | 2204134 A1 | 7/2010 |
| WO | WO-9101772 | 2/1991 |
| WO | WO-9525472 | 9/1995 |
| WO | WO-9736548 A1 | 10/1997 |
| WO | WO-0122897 A1 | 4/2001 |
| WO | WO-0170114 A1 | 9/2001 |
| WO | WO-0230310 | 4/2002 |
| WO | WO-2004098701 A1 | 11/2004 |
| WO | WO 2004098701 A1 * | 11/2004 |
| WO | WO-2005041748 | 5/2005 |
| WO | WO-2005110528 A1 | 11/2005 |
| WO | WO-2006022790 A1 | 3/2006 |
| WO | WO-2006041847 | 4/2006 |
| WO | WO-2006041881 | 4/2006 |
| WO | WO-2006041881 A2 | 4/2006 |
| WO | WO-2007008954 A2 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008014557 | 2/2008 |
| WO | WO-2008061150 | 5/2008 |
| WO | WO-2008061152 | 5/2008 |
| WO | WO-2008070413 | 6/2008 |
| WO | WO-2010078175 A1 | 7/2010 |
| WO | WO-2012033860 | 3/2012 |

OTHER PUBLICATIONS

U.S. Appl. No. 12/871,457, Wu et al.
U.S. Appl. No. 12/940,922, Gelfand et al.
U.S. Appl. No. 12/996,897, Demarais.
U.S. Appl. No. 13/007,370, Gelfand et al.
U.S. Appl. No. 13/009,748, Beetel et al.
U.S. Appl. No. 12/910,631, Wu et al.
International Search Report and Written Opinion for PCT/US2009/069334; Applicant: Ardian, Inc.; Mailing Date: Mar. 1, 2010, 10 pages.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report, PCT/US04/38498, Mailed Feb. 18, 2005, Applicant: G & L Consulting, LLC, 4 pages.
European Search Report; European Patent Application No. 09156661.2; Applicant: Ardian, Inc.; Date of Mailing: Jul. 23, 2009, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
Ardian Medtronic LLC, International Search Report and Written Opinion dated Nov. 22, 2011, International Application No. PCT/US2011/030496, 15 pages.
Avitall et al., "The Creation of Linear Contiguous Lesions in the Atria with an Expandable Loop Catheter"; Journal of the American College of Cardiology, 1999; vol. 33, No. 4; pp. 972-984, located online at: http://content/onlinejacc.org/cgi/content/full/33/4/972.
Excerpt of Operator's Manual, 110V; Boston Scientific's EPT-1000 XP Cardiac Ablation Controller & Accessories, Version of Apr. 2003, (6 pages).
Excerpt of Operator's Manual, 150; Boston Scientific, "Maestro 3000 Cardiac Ablation System", Version of Oct. 17, 2005, Ref. Catalog No. 21020, (4 pages).

(56) References Cited

OTHER PUBLICATIONS

Opposition to European Patent No. EP2092957, Granted Jan. 5, 2011, Date of Opposition Oct. 5, 2011 (26 pages).
Opposition to European Patent No. EP2037840, Granted Dec. 7, 2011, Date of Opposition Sep. 7, 2012 (25 pages).
Opposition to European Patent No. EP1802370, Granted Jan. 5, 2011, Date of Opposition Oct. 5, 2011 (20 pages).
Wittkampf et al., "Control of Radiofrequency Lesion Size by Power Regulation"; Circulation: Journal of the American Heart Association; 1989, vol. 80: pp. 962-968, located online at: http://circ.ahajournals.org/content/80/4/962.
Allen, E.V., Sympathectomy for essential hypertension, Circulation, 1952, 6:131-140.
Bello-Reuss, E. et al., "Effects of Acute Unilateral Renal Denervation in the Rat," J Clin Invest, 1975;56:208-217.
Bello-Reuss, E. et al., "Effects of Renal Sympathetic Nerve Stimulation on Proximal Water and Sodium Reabsorption," J Clin Invest, 1976:57:1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. and Ulla C. Kopp, "Neural Control of Renal Function," Physiological Reviews, vol. 77, No. 1, Jan. 1997, the American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats".
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," in Proceedings of the Society for Experimentla Biology and Medicine, vol. 168, 77-81, 1981. (Abstract).
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency cateheter ablation of accessory pathways in infants." Heart, 78:160-162 (1997).
Dibona, G.F. "Sympathetic nervous system and kidney in hypertension." Nephrol and Hypertension, 11:197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Han, Y.-M, et al., "Renal artery ebolization with diluted hot contrast medium: An experimental study." J Vasc Interv Radiol, 12: 862-868 (2001).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II-21 (1992).
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention in cirrhotic atrial fibrillation." Circulation, 102:2774-2780 (2000).
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Weinstock, M., et al., "Renal denervation prevents sodium rentention and hypertension in salt sensitive rabbits with genetic baroreflex impairment." Clinical Science, 90:287-293 (1996).
Curtis, J.J., et al., "Surgical therapy for presistent hypertension after renal transplantation." Trasnplantation, Feb. 1981, vol. 31, pp. 125-128.
Gelfand, M., et al., "Treatment of renal failure and hypertension" U.S. Appl. No. 60/442,970 dated Jan. 29, 2003.
Krum, et al., "Renal Sympathetic-Nerve Ablation for Uncontrolled Hypertension." New England Journal of Med, Aug. 2009, 361;9.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

(56) References Cited

OTHER PUBLICATIONS

Zheng et al., "Comparison of the temperature profile and pathological effect at unipolar, bipolar and phased radiofrequency current configurations," Journal of Interventional Cardian Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=622732&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988), 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011), 44 pages.
Millard, F. C., et al, "Renal Embolization for ablation of function in renal failure and hypertension." Postgraduate Medical Journal, 65, 729-734, (1989).
Ong, K. L., et al. "Prevalence, Awareness, Treatment, and Control of Hypertension Among United States Adults 1999-2004." Hypertension, 49: 69-75 (2007) (originally published online Dec. 11, 2006).

(56) References Cited

OTHER PUBLICATIONS

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Renal Denervation (RDN), Symplicity RDN System Common Q&A (2011), 4 pages, http://www.medtronic.com/rdn/mediakit/RDN%20FAQ.pdf.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stouffer, G. A. et al., Journal of Molecular and Cellular Cardiology, vol. 62, 2013, 6 pages.

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6 pages, www.clinicaltrials.gov/ct2/show/NCT01390831.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages, http://clinicaltrials.gov/ct2/show/NCT01628198.

Oz, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Schneider, Peter A., "Endovascular Skills—Guidewire and Catheter Skills for Endovascular Surgery," Second Edition Revised and Expanded, 10 pages, (2003), p. 151-152, 198, 284-286.

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Valente, John F. et al., "Laparoscopic Renal Denervation for Intractable ADPKD-Related Pain", Nephrol Dial Transplant (2001) 16: 1 page.

Gelfand, M., et al., "Treatment of renal failure and hypertension." U.S. Appl. No. 60/442,970, 2003, 23 pages.

Curtis, J. J., et al., "Surgical therapy for persistent hypertension after renal transplantation." Transplantation, 1981, 31: 125-128.

International Search Report and Written Opinion for International App. No. PCT/US11/30496, Date Mailed Nov. 22, 2011, 16 pages.

\* cited by examiner

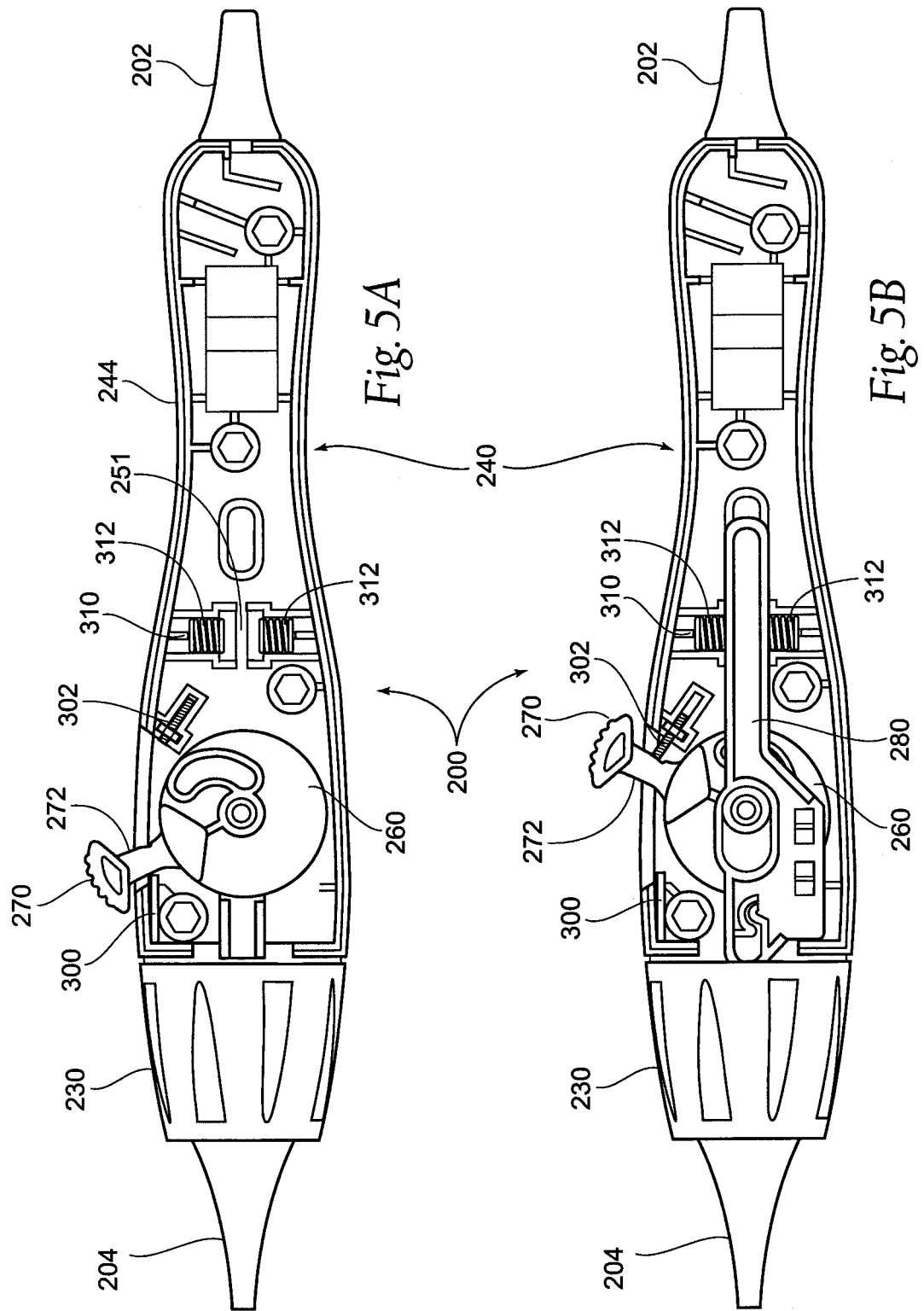

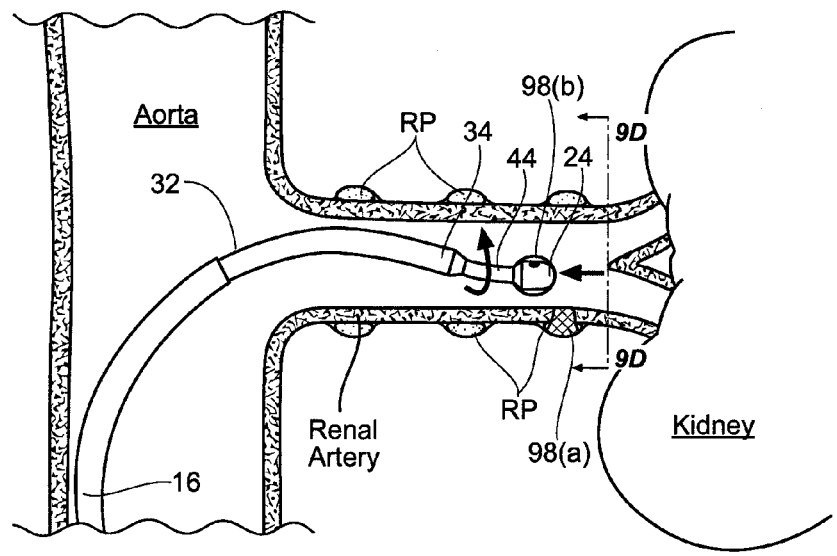
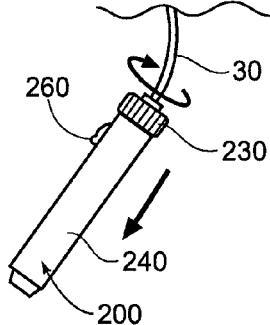
Fig. 9C
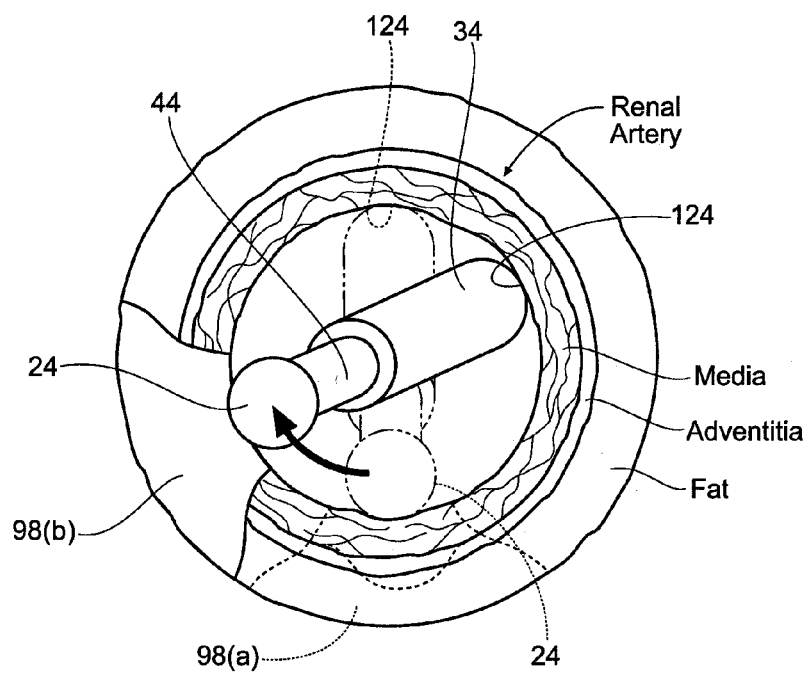
Fig. 9D

HANDLE ASSEMBLIES FOR INTRAVASCULAR TREATMENT DEVICES AND ASSOCIATED SYSTEMS AND METHODS

REFERENCE TO RELATED APPLICATIONS

The present application is a continuation-in-part of Patent Cooperation Treaty (PCT) Application No. PCT/US09/69334, filed Dec. 22, 2009, which claims the benefit of the following applications:

(a) European Patent Application No. 09168202.1 filed Aug. 14, 2009;

(b) European Patent Application No. 09168204.7, filed Aug. 14, 2009;

(c) European Patent Application No. 09167937.3, filed Aug. 14, 2009; and (d) U.S. Provisional Patent Application No. 61/142,128, filed Dec. 31, 2008.

Patent Cooperation Treaty (PCT) Application No. PCT/US09/69334, filed Dec. 22, 2009, is also a continuation-in-part of the following applications:

(e) U.S. patent application Ser. No. 12/545,648, filed on Aug. 21, 2009, now U.S. Pat. No. 8,652,129; and (f) U.S. patent application Ser. No. 12/495,691, filed on Jun. 30, 2009.

All of these applications are incorporated herein by reference in their entireties.

TECHNICAL FIELD

The technology disclosed in the present application generally relates to handle assemblies for intravascular treatment devices and associated systems and methods. In particular, several embodiments are directed to handle assemblies for intravascular treatment devices for achieving intravascular, thermally-induced renal neuromodulation.

BACKGROUND

Hypertension, heart failure and chronic kidney disease represent a significant and growing global health issue. Current therapies for these conditions include non-pharmacological, pharmacological and device-based approaches. Despite this variety of treatment options, the rates of control of blood pressure and the therapeutic efforts to prevent progression of heart failure and chronic kidney disease and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

Reduction of sympathetic renal nerve activity (e.g., via denervation) can reverse these processes. Ardian, Inc., of Palo Alto, Calif., has discovered that an energy field, including and comprising an electric field, can initiate renal neuromodulation via denervation caused by irreversible electroporation, electrofusion, apoptosis, necrosis, ablation, thermal alteration, alteration of gene expression or another suitable modality.

BRIEF DESCRIPTION OF THE DRAWINGS

FIGS. 5A and 5B are side cross-sectional views of the handle assembly of FIGS. 2A-2C and 3A-3E, illustrating optional features for limiting caregiver rotation of the actuator 260 and/or for increasing friction during such caregiver actuation.

FIGS. 9A-9D illustrate the intravascular delivery, placement, deflection, rotation, retraction, repositioning, and use of a treatment device including a handle assembly configured in accordance with an embodiment of the disclosure to achieve thermally-induced renal neuromodulation from within a renal artery.

DETAILED DESCRIPTION

I. Overview

The present disclosure describes handle assemblies for intravascular treatment devices and associated systems and methods.

Although the following description provides many specific details of the following examples in a manner sufficient to enable a person skilled in the relevant art to practice, make, and use them, several of the details and advantages described below may not be necessary to practice certain examples and methods of the disclosure. Additionally, the disclosure may include other examples and methods that are within the scope of the claims but are not described in detail.

Reference throughout this specification to "one example," "an example," "one embodiment" or "an embodiment" means that a particular feature, structure, or characteristic described in connection with the example is included in at least one example of the present disclosure. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the disclosure. The headings provided herein are for convenience only and are not intended to limit or interpret the scope or meaning of the claimed disclosure.

Figure 1:
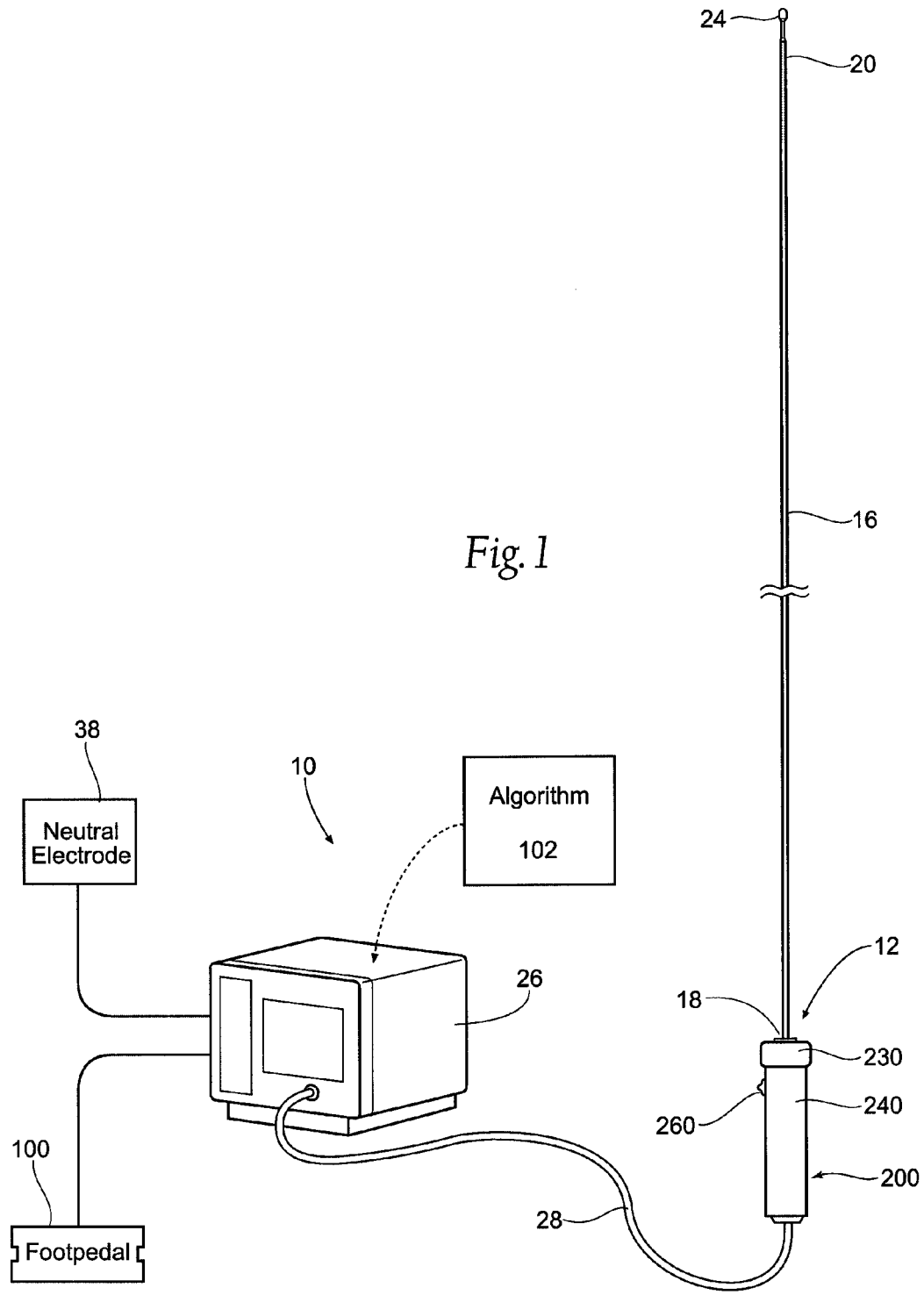
FIG. 1 is a partially schematic view of a system for achieving intravascular, thermally-induced renal neuromodulation.

II. Intravascular Treatment Device Embodiment and Associated System and Methods FIG. 1 shows a system 10 for thermally inducing neuromodulation, e.g., of a left and/or right renal plexus (RP), through intravascular access. The left and/or right renal plexus (RP) surrounds the respective left and/or right renal artery. The renal plexus (RP) extends in intimate association with the respective renal artery into the substance of the kidney. The system may thermally induce neuromodulation of a renal plexus (RP) by intravascular access into the respective left or right renal artery.

Figure 8:
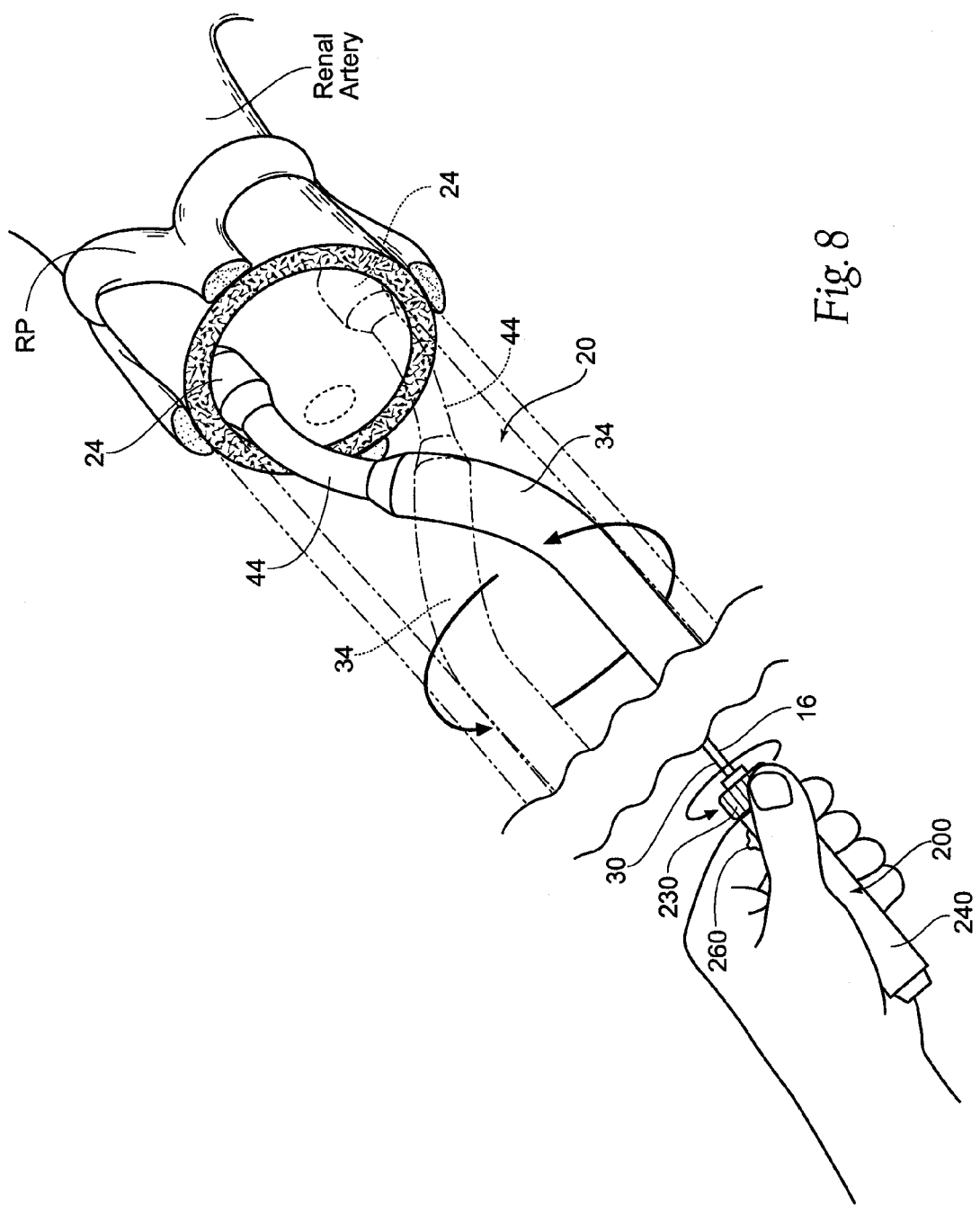
FIG. 8 illustrates operation of the handle assembly to manipulate the treatment device within a renal artery.

The system 10 includes an intravascular treatment device 12. The treatment device 12 includes an elongated shaft 16 having a proximal end region 18 and a distal end region 20. The treatment device 12 provides access, e.g., to the renal plexus (RP), through an intravascular path that leads to a respective renal artery, as FIGS. 8, 9, and 10 show.

Different sections of the elongated shaft 16 serve different mechanical functions when in use. The sections are thereby desirably differentiated in terms of their size, configuration, and mechanical properties for (i) percutaneous introduction into a femoral artery through a small-diameter access site; (ii) atraumatic passage through the tortuous intravascular path through an iliac artery, into the aorta, and into a respective left/right renal artery, including (iii) significant flexure near the junction of the left/right renal arteries and aorta to gain entry into the respective left or right renal artery; (iv) controlled translation, deflection, and/or rotation within the respective renal artery to attain proximity to, and a desired alignment with, an interior wall of the respective renal artery; and (v) the placement of at least one thermal element 24 (e.g., a thermal heating element) carried by the distal end region 20 into contact with tissue on the interior wall. The thermal element 24 is specially sized and configured for manipulation and use within a renal artery.

The proximal end region 18 of the elongated shaft 16 includes a handle assembly 200. The handle assembly 200 is sized and configured to be securely or ergonomically held and manipulated by a caregiver (see, e.g., FIG. 8) positioned external to the patient, outside the intravascular path traversed by the distal end region 20 of the treatment device 12 in accessing a renal artery. By manipulating the handle assembly 200 from outside the intravascular path, the caregiver can advance the elongated shaft 16 through the tortuous intravascular path and remotely manipulate or actuate the distal end region 20. Image guidance, e.g., CT, radiographic, or another suitable guidance modality, or combinations thereof, can be used to aid the caregiver's manipulation.

The distal end region 20 of the elongated shaft 16 can flex in a substantial fashion to gain entrance into a respective left/right renal artery by manipulation of the elongated shaft 16, e.g., via passage within a guide catheter (not shown). Once entrance to a renal artery is gained, further manipulation of the distal end region 20 and the thermal heating element 24 within the respective renal artery establishes proximity to and alignment between the thermal heating element 24 and tissue along an interior wall of the respective renal artery. In some embodiments, manipulation of the distal end region 20 will also facilitate contact between the thermal heating element 24 and wall of the renal artery.

The system 10 also includes a thermal generator 26 (e.g., a thermal energy generator). Under control of the caregiver or automated control algorithm 102, the generator 26 generates a selected form and magnitude of thermal energy. A cable 28 operatively attached to the handle assembly 200 electrically connects the thermal heating element 24 to the generator 26. At least one supply wire 29 (see, e.g., FIG. 3A) passing along the elongated shaft 16 or through a lumen in the elongated shaft 16 from the handle assembly 200 to the thermal heating element 24 conveys the treatment energy to the thermal heating element 24. A control mechanism, such as foot pedal 100, optionally is connected (e.g., pneumatically connected or electrically connected) to the generator 26 to allow the operator to initiate, terminate and, optionally, adjust various operational characteristics of the generator, including, but not limited to, power delivery.

For systems that provide for the delivery of a monopolar electric field via the thermal heating element 24, a neutral or dispersive electrode 38 can be electrically connected to the generator 26. Additionally, one or more sensors 52 (see FIG. 9), such as one or more temperature (e.g., thermocouple, thermistor, etc.), impedance, pressure, optical, flow, chemical or other sensors, can be located proximate to or within the thermal heating element 24 and connected to one or more of the supply wires. With two supply wires, one wire could convey the energy to the thermal heating element and one wire could transmit the signal from the sensor. Alternatively, both wires could transmit energy to the thermal heating element.

As seen in FIGS. 8 and 9 (and described in more detail below), a caregiver may manipulate the distal end region 20 of elongated shaft 16 into a desired intravascular position by manipulating handle assembly 200 that is positioned external to the patient outside the intravascular path traversed by the distal end region. The elongated shaft 16 may comprise force transmitting section 30 that transmits forces from the handle assembly 200 to the distal end region 20. Distal end region 20 may comprise proximal flexure zone 32 that accommodates significant flexure at the junction of the left/right renal arteries and aorta to gain entry into the respective left or right renal artery. Furthermore, the distal end region may comprise intermediate flexure zone 34. Utilizing handle assembly 200, the intermediate flexure zone can be axially translated into the respective renal artery, remotely deflected and/or rotated in a controlled fashion within the respective renal artery to attain proximity to and a desired alignment with an interior wall of the respective renal artery. The distal end region also may comprise distal flexure zone 44 that passively bends to place the thermal energy heating element 24 into contact with tissue on the interior wall of the respective renal artery.

The complex, multi-bend structure formed by the proximal, intermediate and distal flexure zones 32, 34, and 44 of the distal end region 20 of the elongated shaft 16 create a consistent and reliable active surface area of contact between the thermal heating element 24 and tissue within the respective renal artery. Once proximity between, alignment with, and contact between the thermal heating element 24 and tissue are established within the respective renal artery, the purposeful application of energy from the generator 26 to tissue by the thermal heating element 24 induces one or more desired thermal heating effects on localized regions of the renal artery and adjacent regions of the renal plexus (RP), which lay intimately within or adjacent to the adventitia of the renal artery. The purposeful application of the thermal heating effects can achieve neuromodulation along all or a portion of the RP.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

III. Handle Assemblies for Intravascular Treatment Devices and Associated Systems and Methods With reference to FIG. 2A, an illustrative embodiment of the handle assembly 200 of system 10 is described. With the handle assembly 200 positioned external to the patient, the caregiver can translate the handle assembly to translate the distal end region 20 of the elongated shaft 16 through an intravascular path to a position within the respective renal artery. The caregiver then can operate actuator 260 of the handle assembly 200 to remotely deflect the thermal heating element 24 about the intermediate flexure zone 34 to establish contact between the interior wall of the renal artery and the thermal heating element. The caregiver also can operate rotator 230 on the handle assembly 200 to rotate the elongated shaft 16 and its distal end region 20 without rotating the entire handle assembly 200.

Rotation of the elongated shaft 16 when the intermediate flexure zone 34 is deflected within the respective renal artery causes the thermal heating element 24 to rotate within the respective renal artery, making it easier to achieve contact with the vessel wall, to determine whether there is wall contact (particularly in planes where there is poor angiographic visualization), and/or to angularly reposition the thermal heating element. Rotation may be combined with translation of the thermal heating element 24 for repositioning of the thermal heating element at a different angular and longitudinal position within the respective renal artery for delivery of energy at multiple locations within the renal artery. Since there are cables and wires running from the handle assembly through the shaft of the device (e.g., actuation wire/cable, electrical transmission wire(s), thermocouple wire(s), etc.), it is desirable to limit rotation of the shaft relative to these wires in order to avoid unnecessary entanglement and twisting of these wires; handle assembly 200 therefore comprises a rotational limiting element, as described in more detail below.

Figure 2A:
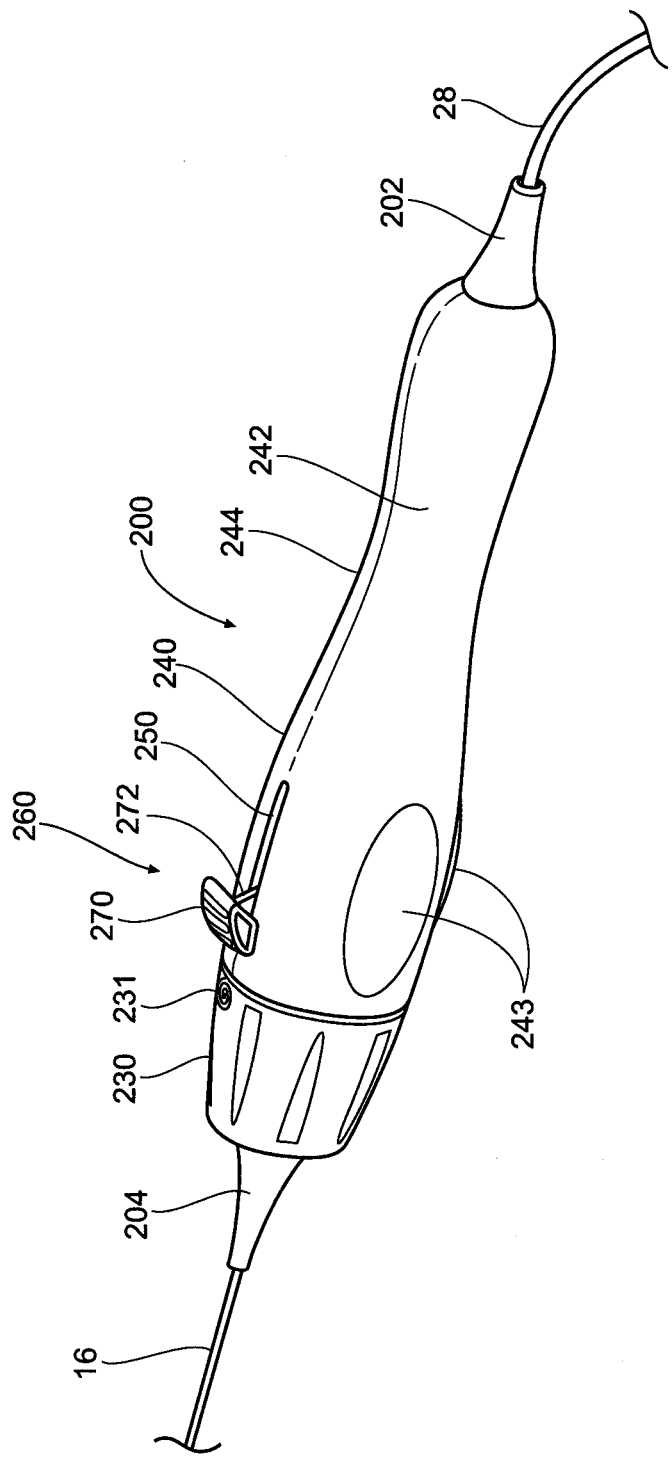
FIG. 2A is an isometric view of a handle assembly for a treatment device configured in accordance with an embodiment of the disclosure.
Figure 2B:
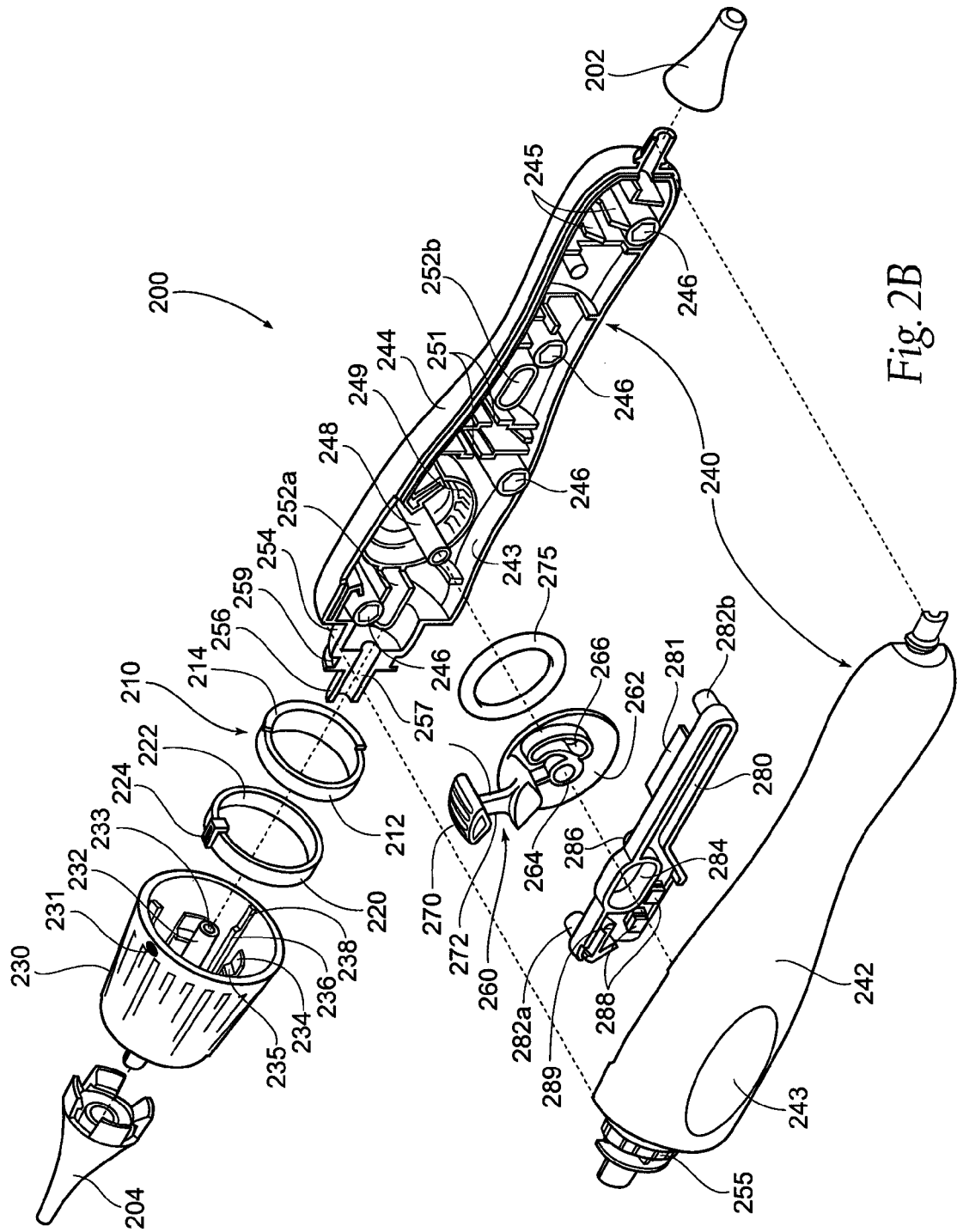
FIG. 2B is an exploded isometric view of the handle assembly of FIG. 2A.

As seen in the exploded view of FIG. 2B, handle assembly 200 may comprise proximal strain relief 202, distal strain relief 204, inner limiter ring 210, outer limiter ring 220, rotator 230, housing assembly 240 having upper housing 242 and lower housing 244, actuator 260 and carrier 280, as well as optional O-ring 275. The upper and lower housing comprise one or more mating features 246 that join together (e.g., via friction locked male and female mating features and/or via adhesives) to form the handle housing assembly 240. The actuator, O-ring and carrier are positioned between the upper housing 242 and lower housing 244 in the assembled configuration of housing assembly 240.

As described in more detail below, in the assembled configuration the actuator 260 and carrier 280 are constrained within the housing assembly 240 in a manner that facilitates coordinated angular rotation of the actuator and linear translation of the carrier. As also described in more detail below, proximal linear translation of carrier 280 relative to the housing assembly 240, via caregiver proximal rotation of actuator 260, causes deflection of thermal heating element 24 about intermediate flexure zone 34 of the distal end region 20 of the elongate shaft 16. Optional O-ring 275, positioned between the actuator 260 and the lower housing 244, may provide tactile feedback or resistance to the caregiver during such caregiver rotation of the actuator, and/or may maintain the actuator in proximally rotated position. An alternative actuation mechanism can include a sliding actuator directly or indirectly connected to a control wire, wherein caregiver sliding of the sliding actuator causes linear translation of the control wire relative to the housing assembly and deflection of the thermal heating element about the intermediate flexure zone. Yet another alternative actuation mechanism can include a rotational actuator directly or indirectly connected to a control wire, wherein caregiver rotating of the rotating actuator causes linear translation of the control wire relative to the housing assembly and deflection of the thermal heating element about the intermediate flexure zone.

After assembly of the housing 240, the inner limiter ring 210 is positioned concentrically over a distal portion of the housing assembly 240, the outer limiter ring 220 is positioned concentrically over the inner limiter ring 210, and the rotator is positioned concentrically over the outer limiter ring 220. Proximal strain relief 202 is affixed to a proximal portion of the housing assembly 240, while distal strain relief 204 is affixed to a distal portion of the rotator 230. As described in more detail below, the inner limiter ring 210, the outer limiter ring 220 and the rotator 230 act in concert with the housing assembly 240 to facilitate rotation of elongated shaft 16 without rotation of the handle assembly 200, as well as to limit rotation of the elongated shaft.

Treatment device 12 comprises control wire 40 that extends the length of elongated shaft 16 (e.g., along the length or within a lumen of the elongated shaft) from the handle assembly 200 of proximal end region 18 to the intermediate flexure zone 34 of the distal end region 20. The control wire terminates distally in the distal end region 20 and, as seen in FIG. 3, terminates proximally at carrier 280 of the handle assembly 200. As discussed in more detail below, the control wire may be attached to the carrier 280 by simply being wrapped around one or more cleats or attachment points on the carrier and/or attachment via adhesive or solder. Proximal translation of the carrier 280 relative to housing assembly 240 (and thereby relative to the elongated shaft 16) proximally retracts the control wire relative to the elongated shaft 16, which imparts a bending moment on the intermediate flexure zone 34 that causes the intermediate flexure zone to bend or deflect relative to a longitudinal axis of the elongated shaft 16. This facilitates positioning of the thermal heating element 24 in a desired location relative to a respective renal artery.

Optionally, the control wire 40 may be elastic and/or may be connected to an elastic element, such as a spring, to dampen the force applied to the control wire by translation of the carrier 280, thereby dampening the buckling or bending moment applied to the intermediate flexure zone 34. This may provide a more consistent contact force between the thermal heating element 24 and the vessel wall. It also may facilitate maintenance of stable contact as the vessel wall moves relative to the elongated shaft.

By rotating the actuator 260 proximally, the caregiver may proximally translate the carrier 280 relative to the housing assembly 240 in order to proximally retract the control wire 40 relative to the elongated shaft 16, thereby deflecting the intermediate flexure zone 34 of the distal end region 20. Actuator 260 comprises an actuator body 262 having a pivot 264, as well as a cam 266 that is positioned on the surface of the actuator that faces upper housing 242 and carrier 280 in the assembled configuration.

Actuator 260 also has as an actuator button 270 that is coupled to the actuator body via an actuator button arm 272. The actuator button arm 272 acts as a lever arm that provides additional torque and mechanical advantage during rotation of the actuator 260. The actuator button 270 optionally has a larger width than the actuator button arm 272 to facilitate tactile manipulation and ergonomic handling of the actuator button by a caregiver. The actuator button 270 initially is positioned in a forward or distal position relative to housing assembly 240. The caregiver may pull back (i.e. proximally) on the button 270 to proximally rotate the actuator 260 relative to the housing assembly and deflect the intermediate flexure zone 34 of the distal end region 20. The range of distances separating the actuator button 270 from the rotator 230 during caregiver manipulation of the handle assembly 200 is specified in a manner that facilitates single-handed ergonomic use of the handle assembly 200, even when the actuator button 270 is positioned in its proximal-most or distal-most position relative to the housing assembly 240.

The housing assembly 240 (illustratively, the lower housing 244) comprises an actuator post 248 that is placed within the actuator's pivot 264. The actuator post 248 constrains translation of the actuator 260 relative to the housing assembly 240, while facilitating angular rotation of the actuator about the actuator post 248 and the actuator's pivot 264, which is the actuator's axis of rotation. The actuator post 248 facilitates proper alignment of the actuator 260 relative to the housing assembly 240 and the carrier 280, and may reduce a risk of actuator binding during angular rotation of the actuator. The actuator post 248 also may comprise a mating feature 246 of the housing assembly 240.

Upon mating of the upper housing 242 and the lower housing 244 to form the housing assembly 240, actuator button arm 272 of the actuator 260 is seated within the actuator channel 250 formed through the mating of the upper and lower housings (see FIG. 2A). Actuator channel 250 provides the caregiver with access to the actuator button 270 from outside the housing assembly 240, allowing the caregiver to rotate the actuator 260 relative to the housing assembly via the actuator button while the actuator body 262 is disposed within the housing assembly. Carrier 280 is also positioned within the housing assembly; the carrier interacts with the actuator 260 and the housing assembly 240 to transform rotation of the actuator into translation of the carrier relative to the housing assembly, and thereby translation of the control wire 40 relative to the elongated shaft 16.

Figure 3A:
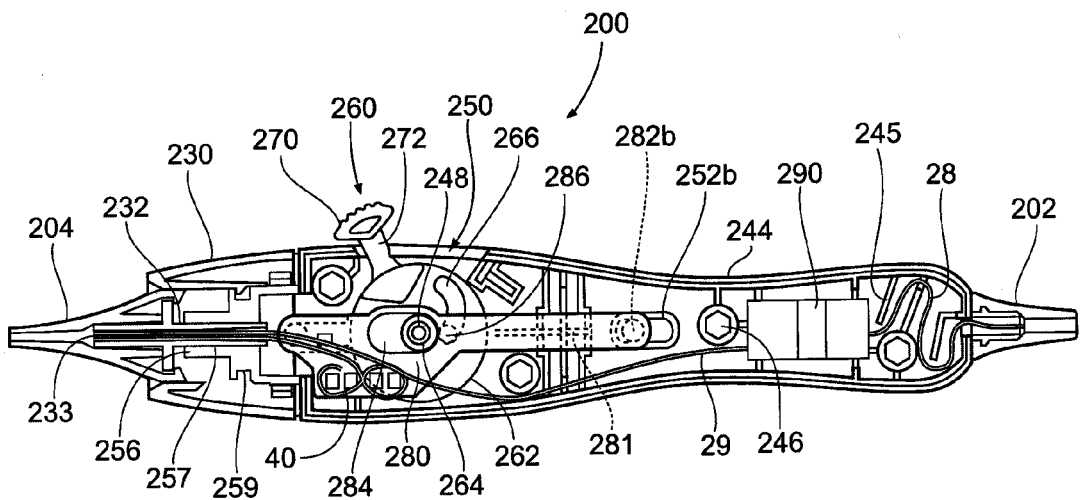
FIGS. 3A and 3B are side cross-sectional views of the handle assembly of FIG. 2A.
Figure 3B:
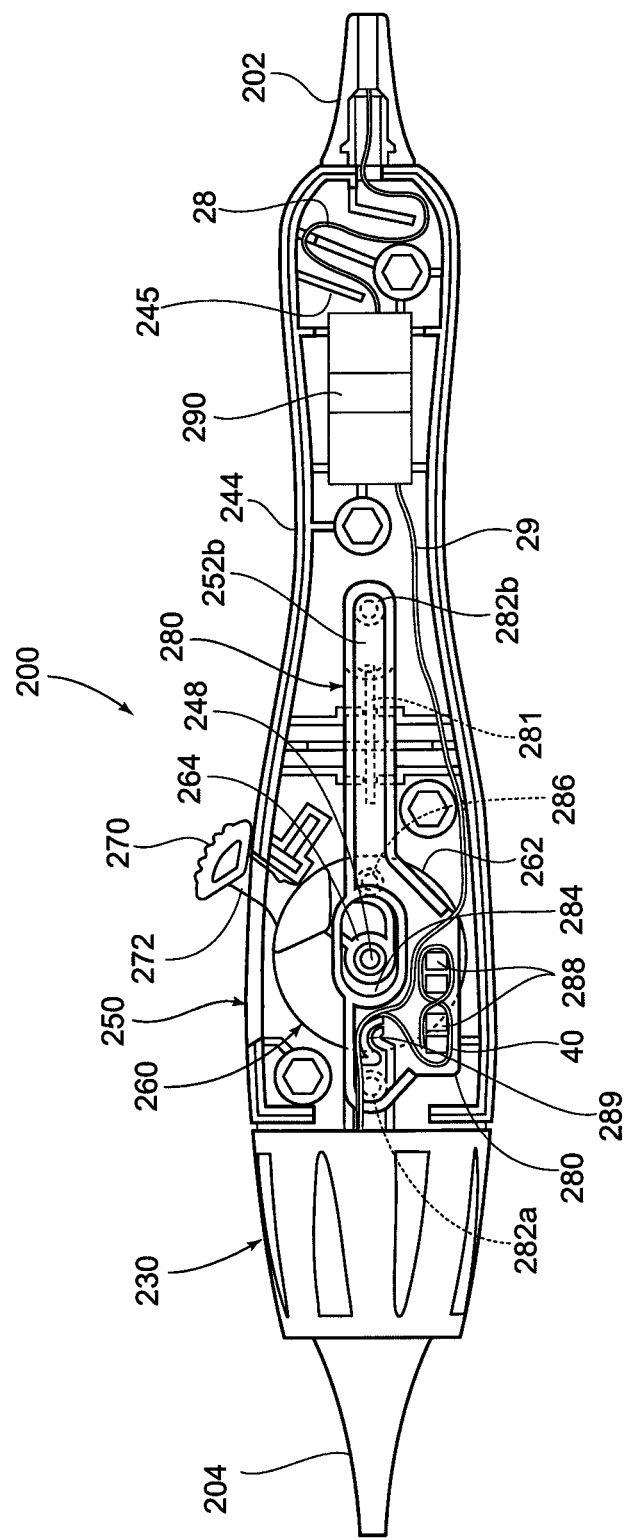
Figure 3C:
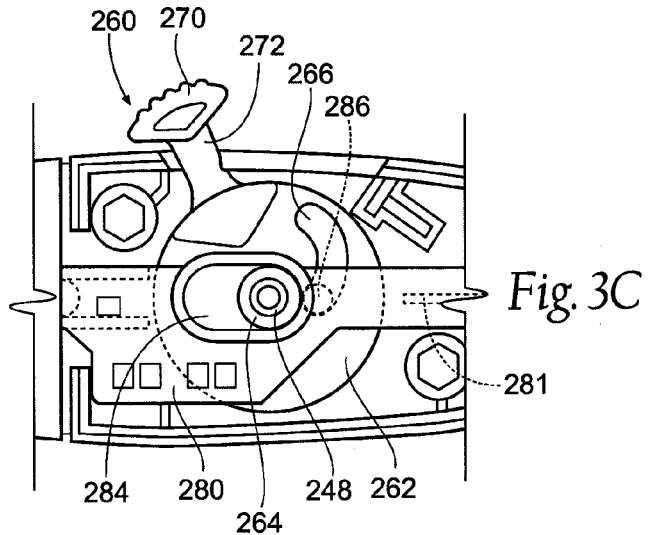
FIGS. 3C-3E provide detail side cross-sectional views of the handle assembly of FIGS. 3A and 3B, illustrating coordinated angular rotation of the actuator and linear translation of the carrier relative to the housing assembly.

The carrier 280 comprises first and second housing posts 282a and 282b that are positioned within first and second longitudinal channels 252a and 252b, respectively, of the lower housing 244 of housing assembly 240. The carrier 280 also comprises fin 281 that is positioned within channel 251 of the lower housing 244. The carrier comprises a cam post 286 that is seated within the actuator's cam 266. Furthermore, the carrier comprises one or more attachment points or features 288 whereat the control wire 40 is proximally coupled to the carrier 280. As seen in FIG. 3B, as the control wire extends proximally, it may remain axial with the elongated shaft 16 until reaching arcuate segment 289 of the carrier, where the control wire changes directions and is attached to the carrier at carrier attachment points 288. The carrier also may comprise a channel or void 284 for passage of the lower housing's actuator post 248 there through (see FIG. 3) and/or for passage there through of a mating feature 246 that extends from the upper housing 242 and mates with the lower housing's actuator post 248.

Positioning of the carrier's first and second housing posts 282a and 282b within the lower housing's first and second longitudinal channels 252a and 252b, as well the carrier's fin 281 within the lower housing's channel 251, constrains rotation of the carrier 280 relative to the housing assembly 240, while facilitating translation of the carrier relative to a longitudinal axis of the housing assembly. Optionally, interaction of the carrier's first and second housing posts with the housing assembly's first and second longitudinal channels may limit a degree of such longitudinal translation of the carrier relative to the housing assembly as the carrier's housing posts abut the proximal and/or distal ends of the lower housing's longitudinal channels. This, in turn, may limit deflection of the intermediate flexure zone 34 of the distal end region 20 of the elongated shaft 16 via the proximal connection of control wire 40 to the carrier 280 and the distal connection of the control wire to the intermediate flexure zone, and/or may limit rotation of the actuator relative to the housing assembly due to the interaction (described in more detail below) between the carrier's cam post 286 and the actuator's cam 266.

Figure 3D:
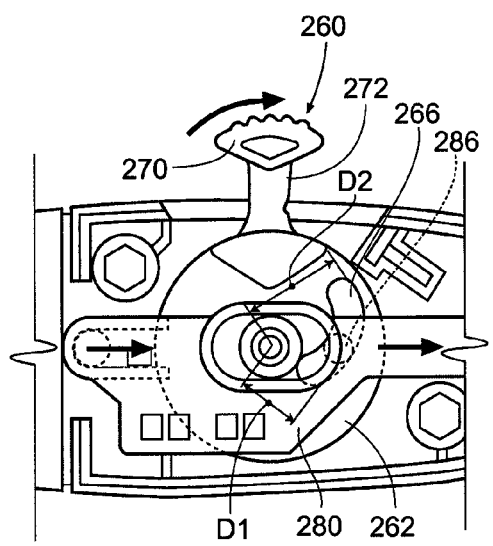
Figure 3E:
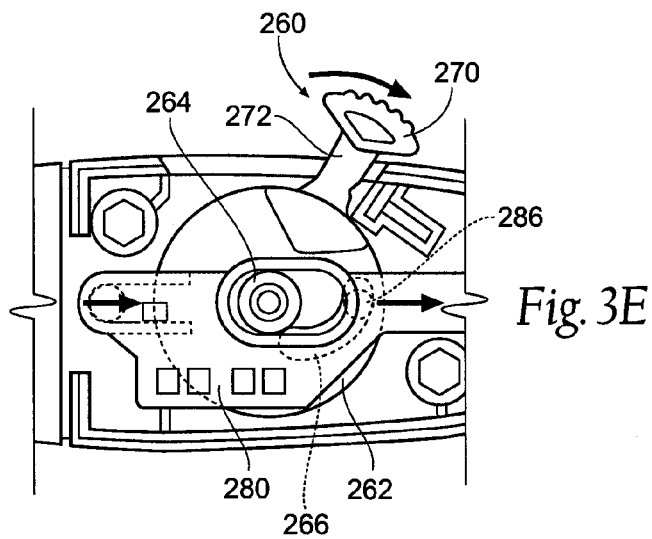

As mentioned, the carrier's cam post 286 is positioned within the actuator's cam 266. When the actuator button 270 is positioned in its distal-most position relative to the housing assembly 240, as in FIG. 3C, the carrier's cam post 286 is positioned at or near an inferior surface of the actuator's cam 266. As the caregiver rotates actuator button 270 proximally relative to the housing assembly, rotation of the actuator 260 causes the carrier's cam post 286 to move toward a superior surface of the actuator's cam 266, as in FIGS. 3D and 3E. As seen in FIG. 3D, a distance D1 between the actuator's axis of rotation (i.e., pivot 264) and the inferior surface of the actuator's cam 266 is less than a distance D2 between the pivot and the superior surface of the cam.

As the carrier's cam post 286 traverses the actuator's cam 266 from inferior to superior during the caregiver's rotation of the actuator button 270 from a more distal position (as in FIGS. 3A and 3C) to a more proximal position (as in FIGS. 3B and 3E) relative to the housing assembly 240, the increased distance between the actuator's pivot 264 and the actuator's cam 266 from inferior to superior causes the actuator's cam 266 to apply a force to the carrier's cam post 286 positioned therein. This force increases the distance between the actuator's pivot 264 and the carrier's cam post 286. Since rotation of the carrier 280 relative to the housing assembly 240 is constrained via interaction of the carrier's first and second housing posts 282a and 282b with the lower housing's first and second longitudinal channels 252a and 252b, the force applied to the carrier's cam post 286 by the actuator's cam 266 during proximal rotation of the actuator 260 relative to the housing assembly 240 translates the carrier proximally relative to the longitudinal axis of the housing assembly. This deflects the intermediate flexure zone 34 of distal end region 20 via tension applied by the carrier to control wire 40.

Conversely, as the carrier's cam post 286 traverses the actuator's cam 266 from superior to inferior during rotation of the actuator button 270 from a proximal position to a distal position relative to the housing assembly 240, the decreased distance between the actuator's pivot 264 and cam 266 from superior to inferior causes the actuator's cam 266 to apply a force to the carrier's cam post 286 positioned therein. This force decreases the distance between the actuator's pivot 264 and the carrier's cam post 286 that is positioned within the actuator's cam 266 and translates the carrier 280 distally relative to a longitudinal axis of the housing assembly 240. Such distal translation of the carrier relative to the housing assembly allows the intermediate flexure zone 34 to straighten via removal of tension applied by the carrier to control wire 40. Alternatively, as the carrier translates distally (e.g., due to a restoring force applied to the carrier by the deflected intermediate flexure zone 34 via the control wire 40), the carrier's cam post 286 may apply a force to the actuator's cam 266 that moves the cam post 286 from superior to inferior within the actuator's cam 266 and rotates the actuator button 270 distally.

As will be apparent to those of skill in the art, the length of the housing assembly's first and/or second longitudinal channels 252a and 252b optionally may limit longitudinal translation of the carrier 280 relative to the housing assembly 240. Furthermore, the difference between the distances D2 and D1 (i.e., D2−D1) optionally may define a maximum translation distance of the carrier 280 relative to the housing assembly 240. Furtherstill, the geometry of the actuator's cam 266 optionally may be altered to alter the amount of linear translation of carrier 280 that results from a given amount of angular rotation of actuator 260, and vice versa.

The geometry of cam 266 optionally may be configured to interact with cam post 286 in a manner that provides variable resistance to the caregiver during rotation of the actuator 260. For example, resistance may increase as the actuator is rotated more proximally. At the limit, such increased resistance may serve as a brake that precludes further proximal rotation of the actuator relative to the housing assembly.

As discussed previously, the control wire 40 extends from the distal end region 20 of elongated shaft 16 to attachment features 288 of the carrier 280. Proximal longitudinal translation of the carrier 280 relative to the housing assembly 240 (i.e., proximal rotation of the actuator 260 relative to the housing assembly) places the control wire 40 in tension, which deflects the intermediate flexure zone 34. Conversely, distal longitudinal translation of the carrier 280 relative to the housing assembly 240 (i.e., distal rotation of the actuator relative to the housing assembly) reduces or eliminates tension in the control wire, which may reduce or eliminate deflection of the intermediate flexure zone 34. A geometric constraint defined by a length of the housing assembly's actuator channel 250, in combination with a distance between the axis of rotation of the actuator 260 and the actuator button arm 272 as it abuts either end of the channel 250, optionally may define a maximum arc length and degree of rotation that may be traversed by the actuator during its rotation about the housing's actuator post 248, which in turn may define a maximum deflection of the intermediate flexure zone 34 of distal end region 20. Alternatively/additionally, a geometric constraint limiting deflection of the intermediate flexure zone 34 may be defined by interaction of the actuator with the carrier 280 (e.g., the carrier's cam post 286 abutting either end of the actuator cam 266), by interaction of the carrier with the housing assembly (e.g., the carrier's first and/or second housing posts 282a and 282b abutting either end of the lower housing's first and/or second longitudinal channels 252a and 252b, respectively, and/or the lower housing's actuator post 248 or a housing mating feature 246 abutting either end of the carrier's channel 284) and/or by a maximum deflection capacity of the intermediate flexure zone 34 of distal end region 20 as conveyed to the handle assembly via control wire 40 attached to the carrier 280.

Figure 2C:
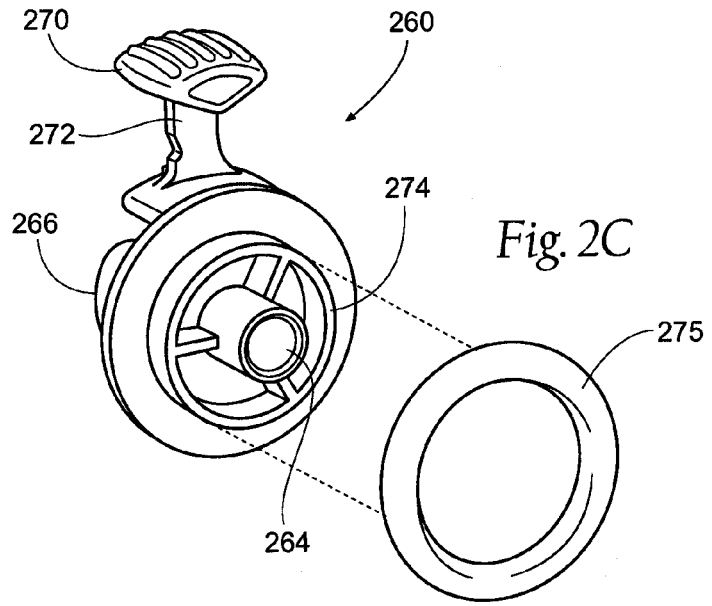
FIG. 2C is a detail isometric view of the actuator and O-ring of the handle assembly of FIG. 2B.

The actuator 260 optionally may comprise male O-ring attachment profile 274 on the surface of the actuator that faces lower housing 244 in the assembled configuration (see FIG. 2C). Profile 274 preferably is concentric with the actuator's pivot 264. The male O-ring attachment profile may have a maximum outer cross-sectional dimension that is just slightly less than the inner diameter of the O-ring 275. The male attachment profile optionally may be slightly non-circular or pointed, e.g., about the ribs of the profile 274.

Likewise, lower housing 244 optionally may comprise optional female O-ring attachment profile 249. The female O-ring attachment profile may have a maximum inner cross-sectional dimension that is just slightly larger than the outer diameter of the O-ring 275. The female attachment profile 249 optionally may be slightly non-circular or pointed, as well, e.g., may have a profile similar to that of the actuator's male attachment profile 274.

Upon mating of the upper housing 242 and the lower housing 244 to form the housing assembly 240, O-ring 275 is positioned within the female O-ring attachment profile 249 of the lower housing 244 and over the male O-ring attachment profile 274 of the actuator 260. With the actuator positioned distally relative to the housing assembly, the non-circular male and female O-ring attachment profiles preferably are concentric, such that the O-ring is in an unstressed state during shipping and storage.

As the actuator button 270 is rotated from a more distal position to a more proximal position within the actuator channel 250, the actuator's male attachment profile 274 is no longer concentric with the lower housing's female attachment profile 249. This may cause engagement of the O-ring 275 between the relatively pointed sections of the actuator's male attachment profile 274 and the lower housing's female attachment profile 249. Such O-ring engagement increases friction, which may provide tactile feedback to the caregiver and/or may provide a friction lock that temporarily maintains the rotational position of the actuator 260 (and thereby the translational position of the carrier 280 and the control wire 40) relative to the housing assembly 240.

As the actuator button 270 is rotated proximally within the actuator channel 250, thereby proximally translating the carrier 280 and deflecting the intermediate flexure zone 34 of the distal end region 20 via the control wire 40, the intermediate flexure zone 34 may convey a restoring moment to the actuator 260 through the control wire and the carrier. The restoring moment may seek to reverse deflection of the intermediate flexure zone and rotate the actuator button 270 back to a more distal position within the actuator channel 250. The increased friction provided by engagement of the O-ring 275 may counteract the intermediate flexure zone's restoring moment to temporarily maintaining deflection of the intermediate flexure zone 34. Alternative friction and locking mechanisms known in the art may be provided.

As discussed previously, cable 28 of system 10 is operatively attached to the handle assembly 200 and electrically connects the thermal heating element 24 at the distal end region 20 of the elongated shaft 16 to the generator 26. The cable 28 may be either removably attached (e.g., via a plug or other cable connector) or permanently attached (e.g., via adhesives and/or solder) to the handle assembly 200. Optionally, the cable may comprise a rotational electrical coupling that facilitates independent rotation of the handle assembly 200 relative to the cable 28. As seen in FIGS. 3A and 3B, cable 28 passes through a proximal lumen of the handle assembly 200 formed through proximal strain relief 202 and the housing assembly 240 into the interior of the handle assembly. The cable 28 terminates within the handle assembly and is electrically connected to at least one supply wire 29. The supply wire(s) convey treatment energy from generator 26 and cable 28 to the thermal heating element 24 and/or transmit signal from one or more sensors 52 (see FIG. 9), such as one or more temperature (e.g., thermocouple, thermistor, etc.), impedance, pressure, optical, flow, chemical or other sensors, located proximate to or within the thermal heating element 24 and connected to the supply wire(s).

In the embodiments of FIG. 3, cable 28 is electrically connected to supply wire(s) 29 via circuit board 290. However, it should be understood that the cable alternatively may be directly connected to the supply wire(s) 29 and/or that the supply wire(s) may extend proximally within the cable 28 proximal of the handle assembly 200, e.g., all the way to the generator 26 without requiring an additional electrical connection to the cable 28. In addition to electrically connecting the supply wire(s) to the cable, circuit board 290 optionally may comprise programming of one or more circuits for controlling, measuring, altering or otherwise interacting with the treatment energy delivered via generator 26 and/or signal transmitted by the supply wire(s) from a distally-located sensor.

In FIG. 3, housing assembly 240 comprises one or more tortuous path features 245 through which cable 28 is routed prior to its termination at circuit board 290. Features 245 may provide sufficient friction to mount cable 28 within the housing assembly 240 without requiring secondary fixation of the cable to the housing, e.g., via adhesives, though it should be understood that secondary fixation alternatively may be provided. Furthermore, other mechanical locks, such as a clip or sleeve that is crimped or otherwise affixed to the cable and is positioned within the housing assembly 240 in a manner that precludes removal of the clip/sleeve from the housing assembly, also may be provided. Circuit board 290 also may be friction fit within the housing assembly and/or may be attached to the housing assembly via secondary fixation, such as adhesives.

Supply wire(s) 29 extend distally from circuit board 290. Along with control wire 40, the supply wire(s) 29 pass through a distal lumen of the handle assembly 200 formed through housing assembly 240, rotator 230 and distal strain relief 204, then along the elongated shaft 16 or through a lumen in the elongated shaft 16 from the handle assembly 200 to the thermal heating element 24. The elongated shaft 16 is coupled proximally to rotator 230 and/or to distal strain relief 204 (and thereby to the rotator).

As will be discussed later in greater detail, it is desirable to rotate the distal end region 20 of the elongated shaft 16 of the treatment device 12 within the renal artery after the thermal heating element 24 is in contact with the vessel wall. However, it may be cumbersome and awkward for a clinical practitioner to rotate the entire handle assembly 200 at the proximal end of the device 12, particularly given the dimensions of the renal anatomy. Rotation of the rotator 230 relative to the housing assembly 240 causes the elongated shaft 16 to rotate about its longitudinal axis without rotation of the handle assembly 200 (i.e., without rotation of the housing assembly 240).

Since control wire 40 and supply wire(s) 29 proximally terminate within the housing assembly 240, significant independent rotation of the elongated shaft relative to the housing assembly might cause the wires to become significantly twisted about one another and/or to break. Optionally, one or more mechanical and/or electromechanical rotational couplings may be provided to connect the more proximal portion of the control wire 40 that is connected to the carrier to the more distal portion of the control wire that travels through the elongated shaft 16, and/or to connect the more distal portions of the supply wire(s) 29 in the elongated shaft 16 to the more proximal portion of the supply wire(s) in the housing assembly 240. Rotational couplings may facilitate independent rotation of the elongated shaft relative to the housing assembly without significant control wire and/or supply wire twisting, while maintaining electrical conductivity along the full length(s) of the supply wires.

Additionally or alternatively, a rotation limiting element may be provided to limit independent rotation of the elongated shaft 16 relative to the handle assembly 200. With reference now to FIGS. 2-4, interactions of the housing assembly 240, the rotator 230, the outer limiter ring 220 and the inner limiter ring 210 are described in more detail. These interactions facilitate independent rotation of the elongated shaft 16 relative to the handle assembly 200, while providing a rotation limiting element that limits such independent rotation, thereby reducing a risk of control and/or supply wire entanglement or breakage.

As discussed previously, the inner limiter ring 210 is positioned concentrically over a distal portion of the housing assembly 240, the outer limiter ring 220 is positioned concentrically over the inner limiter ring 210, and the rotator 230 is positioned concentrically over the outer limiter ring 220. The distal portion of the housing assembly 240 comprises cylindrical segment 254 about which the inner limiter ring 210 is concentrically positioned. The cylindrical segment is of reduced diameter relative to surface 241 of the housing assembly 240 just proximal of the cylindrical segment 254, such that proximal surfaces of the inner limiter ring 210, the outer limiter ring 220 and the rotator 230 abut surface 241 of the housing assembly 240. These abutments may constrain proximal translation of the inner limiter ring 210, the outer limiter ring 220 and/or the rotator 230 relative to the housing assembly 240.

An inner diameter of inner limiter ring 210 is just slightly greater than an outer diameter of the housing assembly's cylindrical segment 254, such that the inner limiter ring may rotate concentrically about the cylindrical segment. Likewise, an inner diameter of outer cylindrical segment 222 of outer limiter ring 220 is just slightly greater that an outer diameter of inner cylindrical segment 212 of the inner limiter ring 210, such that the outer limiter ring may rotate concentrically about the inner limiter ring. Finally, an inner diameter of a proximal region of the rotator 230 is just slightly greater than an outermost diameter of the outer limiter ring 220 at outer tab 224, such that the rotator may rotate concentrically about the outer limiter ring.

The geometric configuration of handle assembly 200 facilitates independent rotation of the rotator 230 relative to the housing assembly 240, while constraining longitudinal translation of the rotator relative to the housing assembly. Via its connection to the rotator, the elongated shaft 16 likewise may be rotated without rotating the handle assembly 200 (i.e., without rotating the housing assembly 240), while translation of the handle assembly also translates the elongated shaft. The distal portion of the housing assembly 240 comprises housing shaft 256 (located distally and of reduced cross-section relative to the housing assembly's cylindrical segment 254) having lumen 257. Rotator 230 comprises rotator shaft 232 having lumen 233 and configured for positioning within the lumen 257 of the housing shaft 256 when the rotator 230 is attached to the housing assembly 240 to facilitate independent rotation of the rotator relative to the housing assembly.

Rotator 230 optionally may comprise one or more rotator elements 234 that engage or rub against cylindrical segment 254 of housing assembly 240 to provide tactile feedback to the caregiver during rotation of the rotator relative to the housing assembly 240. All or a portion of the cylindrical segment 254 optionally may comprise a surface pattern or engagement features 255 that interact with the rotator elements 234 to provide such tactile feedback (see FIGS. 4A and 4B). For example, the surface pattern 255 may comprise alternating segments where the radius of cylindrical segment 254 is slightly increased then decreased. As the caregiver rotates the rotator 230, resistance slightly increases while the rotator elements 234 traverse the increased diameter segments and slightly decreases while the rotator elements 234 traverse the decreased diameter segments. These alternating segments of the surface pattern 255 may traverse known angular segments about the circumference of the cylindrical segment 254. The caregiver may monitor the tactile feedback provided during rotation of the rotator elements 234 about the alternating segments of the surface pattern 255 to monitor the degree of angular rotation of the elongated shaft 16. In one representative embodiment, the surface pattern 255 provides tactile feedback (e.g., transitions between alternating segments of increased and decreased diameter) every 45 degrees of relative rotation between the housing assembly 240 and the rotator 230, though such tactile feedback alternatively may be provided at any other desired degree of relative rotation.

The rotator elements 234 additionally or alternatively may abut and constrain distal translation of the inner limiter ring 210 and/or outer limiter ring 220 relative to the rotator 230, thereby limiting distal translation of the housing assembly 240 relative to the rotator. Translation of the housing assembly 240 relative to the rotator 230 additionally or alternatively may be constrained via engagement elements 235 that extend radially inward from rotator elements 234 and sit within reduced diameter cylindrical channel 259 of the housing assembly's cylindrical segment 254. The engagement elements 235 may comprise one-way valves that allow the rotator to be press fit over the housing assembly with the engagement elements 235 locking into position within the cylindrical channel 259. The engagement elements 235 facilitate rotation of the rotator relative to the housing assembly while constraining proximal (and optionally distal) translation of the housing assembly relative to the rotator.

As another technique for limiting proximal translation of the housing assembly relative to the rotator, a portion of the rotator shaft 232 optionally may flare slightly, while a distal portion of the housing shaft lumen 257 may be of reduced cross-section relative to a more proximal section of the lumen (not shown). The rotator shaft flaring may be of equal or just slightly greater cross-section than the reduced cross-section portion of the housing shaft lumen. During assembly of the handle 200, as the rotator 230 is coupled to the housing assembly 240 with the rotator shaft 232 positioned within the lumen 257 of the housing shaft 256, the rotator shaft flaring may engage and exert friction on the reduced cross-section portion of the housing shaft lumen 257. Continued distal advancement of the reduced cross-section portion of the housing shaft lumen 257 relative to the flaring of the rotator shaft 232 during assembly of the handle 200 may position the reduced cross-section portion of the housing shaft lumen distally of the rotator shaft flaring. In this configuration, the rotator shaft flaring may act as a press fit that constrains proximal translation of the housing assembly 240 relative to the rotator 230, while still allowing the rotator 230 to rotate relative housing assembly 240, i.e., via rotation of the rotator shaft 232 positioned within the lumen 257 of the housing shaft 256.

Distal translation of the housing assembly 240 relative to the rotator 230 may be constrained in a variety of ways, including those already mentioned. As another example, a distal end of the housing shaft 256 may abut a distal portion of the rotator 230. Alternatively or additionally, a proximal region of the rotator 230 may abut surface 241 of the housing assembly 240. As yet another example, an inner surface of the rotator may comprise one or more features or ridges 236 that extend radially inward from an inner surface of the rotator; the ridges may abut a distal surface of outer limiter ring 220 and/or inner limiter ring 210 to limit distal translation of the outer and/or inner limiter ring relative to the rotator 230, thereby limiting distal translation of the limiter rings and the housing assembly 240 relative to the rotator 230.

Figure 4A:
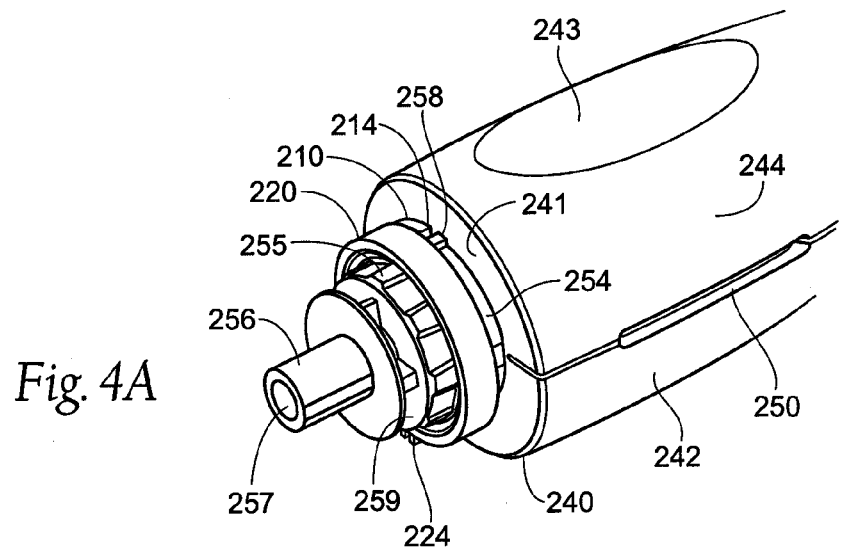
FIG. 4A is an isometric view of a front portion of the handle assembly of FIG. 2A.

Rotation of the elongated shaft 16 relative to the handle assembly 200 may be limited in a variety of ways, e.g., may be limited to a predetermined or optimal number of rotations of the elongated shaft relative to the handle assembly in a variety of ways. In FIGS. 2-4, elongated shaft rotation limitation is achieved via housing nub 258 disposed on cylindrical segment 254 and abutting surface 241 of the housing assembly 240 (see FIG. 4A), via inner arc tab 214 of inner limiter ring 210 that extends both radially outward and longitudinally proximal of inner cylindrical segment 212 of the inner limiter ring, via outer tab 224 of outer limiter ring 220 that extends radially outward and longitudinally along the length as well as proximal of outer cylindrical segment 222 of the outer limiter ring, and via rotator tab 238 that extends radially inward from an inner wall of rotator 230 at or near a proximal end of the rotator.

As described in more detail below, caregiver rotation of the rotator 230 relative to the housing assembly 240 may cause the rotator tab 238 to abut outer tab 224, limiting further rotation of the rotator relative to the outer limiter ring 220; may cause the outer tab 224 to abut the inner arc tab 214, limiting further rotation of the outer limiter ring relative to the inner limiter ring 210; and may cause the inner arc tab 214 to abut the housing nub 258, limiting further rotation of the inner limiter ring relative to the housing assembly 240 and thereby limiting further rotation of the rotator relative to the housing assembly. As the elongated shaft 16 is coupled to the rotator 230, rotation of the elongated shaft relative to the handle assembly is thus also limited.

Figure 4B:
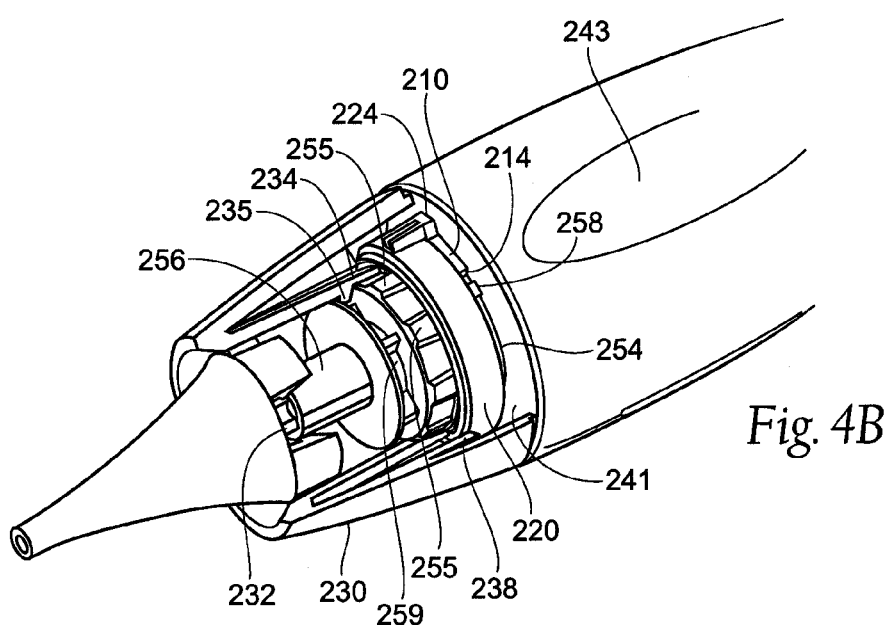
FIG. 4B is an isometric view of a number of internal components at the front portion of the handle assembly.

As best seen in FIGS. 3A and 4B, in the assembled configuration of handle 200 (i.e., with inner limiter ring 210 positioned concentrically about cylindrical surface 254 of housing assembly 240, outer limiter ring 220 positioned concentrically about the inner limiter ring, and rotator 230 positioned concentrically about the outer limiter ring), inner arc tab 214 of inner limiter ring 210, outer tab 224 of outer limiter ring 220 and rotator tab 238 of rotator 230 abut surface 241 of housing assembly 240. As discussed previously, the inner diameter of inner limiter ring 210 is just slightly greater than the outer diameter of the cylindrical segment 254 of housing assembly 240 about which the inner limiter ring is concentrically positioned, facilitating rotation of the inner limiter ring relative to the housing assembly. However, when the inner arc tab 214 that extends longitudinally proximal of the inner cylindrical segment 212 of the inner limiter ring 210 is in rotational alignment with housing nub 258 that extends radially outward from cylindrical surface 254 of the housing assembly 240, the inner arc tab abuts the housing nub; this abutment constrains further rotation of the inner limiter ring relative to the housing assembly. Note that housing nub 258 on cylindrical segment 254 of housing assembly 240 does not extend radially outward to such a degree that it interacts with outer limiter ring 220 or with rotator 230 (i.e., the housing nub does not extend beyond the outer diameter of the inner cylindrical segment 212 of the inner limiter ring 210).

As also discussed previously, the inner diameter of the outer cylindrical segment 222 of the outer limiter ring 220 is just slightly greater than the outer diameter of the inner cylindrical segment 212 of the inner limiter ring 210 about which the outer cylindrical segment of the outer limiter ring is concentrically positioned, facilitating rotation of the outer limiter ring relative to the inner limiter ring. However, the outermost diameter of inner limiter ring 210 at inner arc tab 214 is greater than the outer diameter of the inner cylindrical segment 212 of the inner limiter ring (specifically, the outermost diameter of the inner limiter ring 210 at the inner arc tab 214 is roughly equal to the outer diameter of the outer cylindrical segment 222 of the outer limiter ring 220; thus, the inner arc tab does not interact with the rotator 230). Thus, when the outer limiter ring's outer tab 224, which extends longitudinally along and proximal of the outer limiter ring's outer cylindrical segment 222, is in rotational alignment with the inner arc tab 214 of the inner limiter ring 210, the inner limiter ring's inner arc tab 214 abuts the outer limiter ring's outer tab 224; this abutment constrains further rotation of the outer limiter ring relative to the inner limiter ring.

Again, as discussed previously, the inner diameter of a proximal region of rotator 230 is just slightly greater than the outermost diameter of the outer limiter ring 220 at outer tab 224, facilitating rotation of the rotator relative to the outer limiter ring. The outer diameter of the outer cylindrical segment 222 of the outer limiter ring 220 is less than the outermost diameter of the outer limiter ring 230 at outer tab 224. Rotator tab 238, which may extend longitudinally proximal from one of the ridges 236 on the inner surface of the rotator 230, extends radially inward from the inner surface of the rotator 230. The innermost diameter of the rotator 230 at the rotator tab 238 is smaller than the outermost diameter of the outer limiter ring 220 at the outer tab 224, but larger than the outer diameter of the outer cylindrical segment 222 of the outer limiter ring 220. Thus, when the rotator's rotator tab 238 is in rotational alignment with the outer limiter ring's outer tab 224, the rotator tab abuts the outer tab; this abutment constrains further rotation of the rotator 230 relative to the outer limiter ring 220.

Note that rotator tab 238 does not extend radially inward to the same extent as the ridges 236 of rotator 230. As such, whereas a distal surface of the cylindrical segment 222 of the outer limiter ring 220 may abut the ridges 236 in the assembled configuration of the handle 200, the outer cylindrical segment may be positioned within the rotator 230 concentric with the rotator tab 238. However, the outermost radius of the outer limiter ring 220 at outer tab 224 is such that rotation of the rotator 230 relative to the outer limiter ring until the rotator tab 238 is aligned with the outer tab 224 causes the rotator tab to abut the outer tab, thereby limiting further rotation of the rotator 230 relative to the outer limiter ring 220.

The abutments of rotator tab 238 of rotator 230 with outer tab 224 of outer limiter ring 220, of outer tab 224 with inner arc tab 214 of inner limiter ring 210, and of inner arc tab 214 with housing nub 258 of cylindrical segment 254 of housing assembly 240, limit rotation of the rotator 230 relative to the housing assembly 240. Continued caregiver rotation of the rotator 230 in a given direction relative to the housing assembly 240 causes the rotator tab 238 to abut outer tab 224, limiting further rotation of the rotator in the given direction relative to the outer limiter ring 220; causes the outer tab 224 to abut the inner arc tab 214, limiting further rotation of the outer limiter ring in the given direction relative to the inner limiter ring 210; and causes the inner arc tab 214 to abut the housing nub 258, limiting further rotation of the inner limiter ring in the given direction relative to the housing assembly 240 and thereby limiting further rotation of the rotator in the given direction relative to the housing assembly. Since the elongated shaft 16 is coupled to the rotator 230, rotation of the elongated shaft relative to the handle assembly is thus also limited.

The rotator 230 can rotate approximately one full revolution in a given direction before rotator tab 238 abuts the outer tab 224 of the outer limiter ring 220. Continued rotation of the rotator 230 in the given direction rotates the outer limiter ring 220 with the rotator until the outer limiter ring's outer tab 224 abuts the inner arc tab 214 of the inner limiter ring 210. Further continued rotation of the rotator 230 in the given direction rotates both the outer limiter ring and the inner limiter ring with the rotator until the inner arc tab 214 abuts the housing nub 258 of cylindrical surface 254 of the housing assembly 240, precluding any further rotation of the rotator in the given direction. Rotation of the rotator in the opposite direction can proceed for an equivalent number of revolutions before rotation is limited in that opposite direction.

The degree of rotation of the outer limiter ring 220 relative to the inner limiter ring 210, and of the inner limiter ring 210 relative to the housing assembly 240 is determined by the arc length of the inner arc tab 214 of the inner limiter ring 210. In the embodiment of FIGS. 2-4, the inner arc tab comprises an arc length of approximately 180°. As such, the outer limiter ring may rotate approximately ½ revolution relative to the inner limiter ring, and the inner limiter ring can rotate approximately ½ revolution relative to the housing assembly. Thus, rotation of the rotator 230 (and thereby the elongated shaft 16) relative to the housing assembly 240 is limited to approximately two full revolutions.

As will be apparent to those of skill in the art, by varying the arc length of the inner arc tab 214, the number of full revolutions of the rotator 230 relative to the housing assembly 240 may be varied to any desired degree between about 1 and 3 full revolutions (an arc length close to 360° would limit full rotations to about 1 rotation, while an arc length close to 0° would allow nearly 3 full rotations). As also will be apparent to those of skill in the art, the number of revolutions may be further expanded by utilizing additional limiter rings and tabs.

As best seen in FIG. 2A, rotator 230 optionally may comprise visual indicator 231 that may, for example, be radially aligned with thermal element 24 at distal end region 20 of elongated shaft 16. The caregiver may use visual indicator 231 to monitor the orientation of thermal element 24 and/or to monitor the degree of rotation of the thermal element.

Referring now to FIG. 5, handle assembly 200 may comprise one or more optional features for limiting caregiver rotation of actuator 260 (and thereby limit translation of carrier 280 and deflection of thermal element 24) and/or for increasing friction to provide tactile feedback or a friction lock during such caregiver actuation. As seen in FIG. 5, housing assembly 240 may comprise hard stop distal shim 300 that engages actuator button arm 272 and limits distal rotation of the actuator 260 (see FIG. 5A). Additionally or alternatively, the housing assembly may comprise adjustable proximal hard stop 302 that may be utilized to dynamically adjust the allowable degree of rotation of actuator 260. In FIG. 5A, adjustable proximal hard stop 302 is not extended and does not limit proximal rotation of the actuator. In FIG. 5B, the stop 302 is extended a desired amount and reduces the achievable degree of proximal rotation of actuator 260.

The housing assembly 240 also may comprise spring brake 310 having a spring 312 (e.g. a cantilevered compression spring) positioned on either side of channel 251 of the lower housing 244. As discussed previously, fin 281 of carrier 280 is positioned within the lower housing's channel 251. When utilizing spring brake 310, the springs 312 positioned on either side of the carrier's fin 281 press against the fin and increase friction during translation of the carrier 280. The magnitude of the friction force (static or sliding) applied to the carrier 280 may be specified as desired, e.g., through material selection of the carrier and the springs to obtain a desired coefficient of friction, through specification of the spring constant(s) of the springs 312 used in spring brake 310, and/or through the relative positioning of spring brake 310 and the carrier's fin 281 (i.e., through specification of the normal force applied to the fin 281). In another embodiment, spring brake 310 may comprise a single spring 312, which may be positioned on either side of lower housing channel 251 and carrier fin 281.

Figure 6:
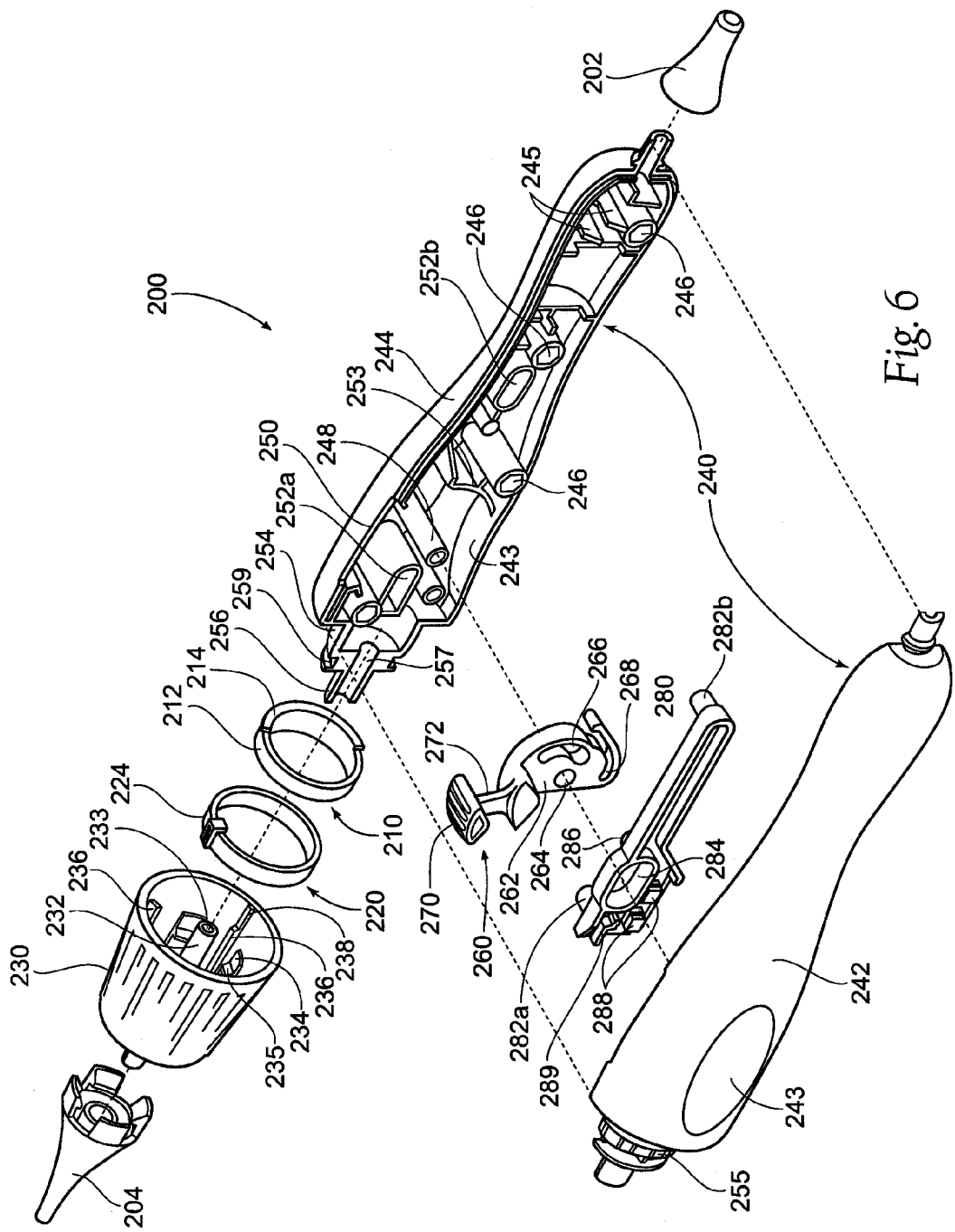
FIG. 6 is an exploded isometric view of an alternative embodiment of the handle assembly of FIGS. 2A-5B having an alternative mechanism for friction generation during caregiver actuation.

With reference to FIG. 6, an alternative embodiment of handle assembly 200 is described having an alternative friction-generating mechanism during caregiver actuation of the actuator 260. In the embodiment of FIG. 6, the handle assembly no longer comprises O-ring 275, the actuator 260 does not have male attachment profile 274, and the lower housing 244 does not have female attachment profile 249. Rather, the actuator 260 comprises friction arm 268 that engages a friction surface 253 of the lower housing 244. As the actuator button 270 is rotated from a more distal position to a more proximal position within the actuator channel 250, the friction arm 268 may engage the housing's friction surface 253, rub against the surface and/or flex to contact the actuator body 262, thereby increasing friction. Increased friction may provide tactile feedback to the caregiver and/or may provide a friction lock that temporarily maintains the rotational position of the actuator 260 (and thereby the translational position of the carrier 280 and the control wire 40) relative to the housing assembly 240.

As the actuator button 270 is rotated proximally within the actuator channel 250, thereby proximally translating the carrier 280 and deflecting the intermediate flexure zone 34 of the distal end region 20 via the control wire 40, the intermediate flexure zone 34 may convey a restoring moment to the actuator 260 through the control wire and the carrier. The restoring moment may seek to reverse deflection of the intermediate flexure zone and rotate the actuator button 270 back to a more distal position within the actuator channel 250. The increased friction provided by engagement of friction arm 268 against friction surface 253 may counteract the intermediate flexure zone's restoring moment to temporarily maintaining deflection of the intermediate flexure zone 34. Additional alternative friction and locking mechanisms known in the art may be provided.

Figure 7A:
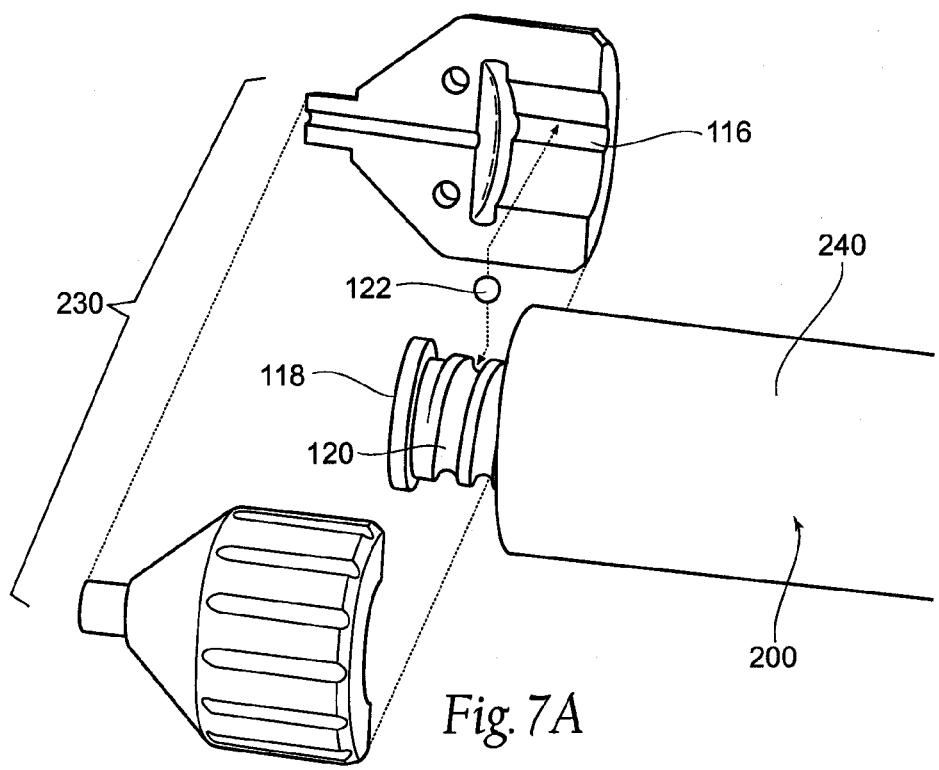
FIGS. 7A and 7B illustrate an alternative rotational limitation element and rotational control mechanism for the handle assembly.
Figure 7B:
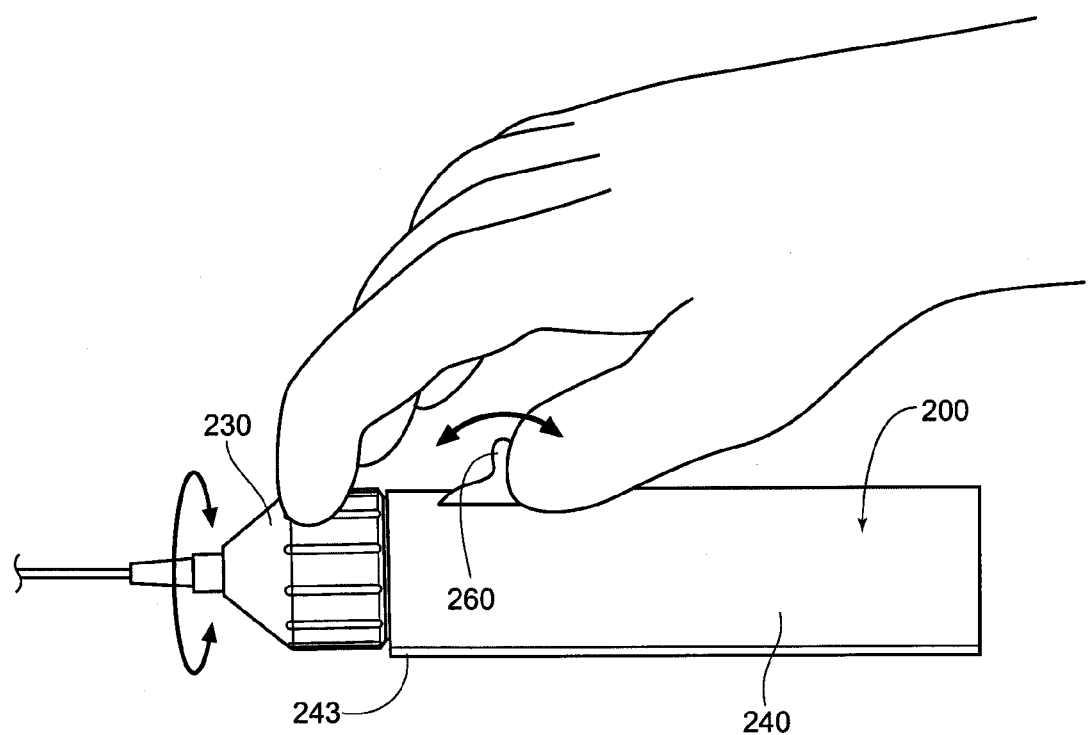

As discussed previously, since there are cables and wires running from the handle assembly 200 through the elongated shaft 16 of the treatment device 12 (e.g., control wire 40, and supply wire(s) 29, such as electrical transmission wire(s), thermocouple wire(s), etc.), it is desirable to limit rotation of the shaft 16 relative to these wires in order to avoid unnecessary entanglement and twisting of these wires. The previously described rotational limiting element of handle assembly 200 addresses this need. FIG. 7 illustrate an alternative rotational limiting element and rotational control mechanism for handle assembly 200.

In the embodiment of FIG. 7, the handle assembly does not comprise inner limiter ring 210 or outer limiter ring 220. Rather, the rotator 230 includes an axial groove 116, and the distal portion of the housing assembly 240 comprises a fitting interface 118 having a helical channel 120. A ball 122 comprising stainless steel or another metal or a polymer is placed within the fitting interface 118 so that it, upon rotation of the rotator, may simultaneously travel within the helical channel 120 of the fitting interface 118 and along the axial groove 116 of the rotator. When the ball 122 reaches the end of the channel and/or groove, the ball will no longer move and, consequently, the rotator will not be able to rotate any further in that direction.

The rotator 230 and the housing assembly 240 can be configured to allow for the optimal number of revolutions for the shaft 16, given structural or dimensional constraints (e.g., wires). The components of the handle may be configured, for example, to allow for two revolutions of the shaft independent of the handle. Limiting rotation of the shaft to the optimal number of revolutions may be achieved, for example, by specifying the linear length of helical channel 120 of housing assembly 240 as a desired fraction or multiple of the inner circumference of rotator 230 in the vicinity of axial groove 116 (e.g., the linear length of helical channel 120 may be about twice the inner circumference of rotator 230 in the vicinity of axial groove 116). Additionally or alternatively, an additional ball 122 (not shown) may be positioned within the axial groove 116 spaced apart from the first ball 122, such that the additional ball travels within the helical channel 120 spaced apart from the first ball. In such an embodiment, the additional ball would limit rotation in one direction when that ball reaches one end of the channel, while the first ball would limit rotation in the other direction when that ball reaches the other end of the channel. In this manner, the two balls would limit rotation of the rotator to an arc length less than would otherwise be provided by the linear length of helical channel 120.

Referring now to FIG. 8, operation of the handle assembly 200 to manipulate the treatment device 12 within a renal artery is briefly described. As has been described and will be described in greater detail later, by intravascular access, the caregiver can manipulate the handle assembly 200 to locate the distal end region 20 of the elongated shaft 16 within the respective renal artery. The caregiver can then operate the actuator 260 on the handle assembly 200 to deflect the thermal heating element 24 about the intermediate flexure zone 34. The caregiver can then operate the rotator 230 on the handle assembly 200 to apply a rotational force along the elongated shaft 16.

The rotation of the elongated shaft 16 when the intermediate flexure zone 34 is deflected within the respective renal artery rotates the thermal heating element 24 within the respective renal artery, making it easier to achieve contact with the vessel wall and determine whether there is wall contact, particularly in planes where there is poor angiographic visualization. Rotation may be combined with translation of the thermal heating element 24 for repositioning of the thermal heating element at a different radial and longitudinal position within the respective renal artery for delivery of energy at multiple locations within the renal artery.

As seen in FIG. 8, the caregiver is able to hold the proximal portion of the handle 200 rotationally stationary in one hand and, with the same or different hand, apply a torsional force to the rotator 230 to rotate the elongated shaft 16. This allows the actuator 260 to remain easily accessed for controlled deflection of the intermediate flexure zone 34 of distal end region 20 of the elongated shaft 16. A rotational limiting element, such as those described previously, limits rotation of the shaft 16 relative to the handle assembly 200 in order to avoid unnecessary entanglement and twisting of the control and supply wires.

In an additional aspect of the disclosed technology, the handle 200 may be configured to minimize operator/caregiver handling of the device while it is within the patient. As shown in FIGS. 2-7, the handle assembly 200 may comprise one or more surfaces 243 that substantially conform to the surface beneath (e.g., operating table). This surface 243, which is shown to be substantially flat in FIGS. 2-7, can alternatively be curved, shaped or angled depending on the configuration and/or geometry of the beneath surface. The conforming surface 243 enables the caregiver to keep the handle assembly 200 stable when the treatment device 12 is within the patient. In order to rotate the device when it is inside the patient, the operator can simply dial the rotator 230 without any need to lift the handle assembly 200. When the operator desires to retract the device for subsequent treatments, the operator can simply slide the handle assembly along the beneath surface to the next position. Again, this mitigates the risk of injury due to operator error or over handling of the treatment device. Additionally or alternatively, the surface 243 can engage the beneath surface using clips, texture, adhesive, etc.

Additional optional enhancements to the rotation mechanism disclosed herein include providing tactile and/or visual feedback on the rotator 230 so that the operator can exercise greater control and care in rotating the device. The rotator 230 also optionally may be selectively locked to the interface, thereby preventing further rotation, if the operator wishes to hold the treatment device in a particular angular position. Furthermore, the rotator 230 optionally may be coupled to the elongated shaft 16 via a rotation gearing mechanism, such that the degree of rotation of the rotator 230 is scaled to create more or less rotation of the elongated shaft 16.

Another optional enhancement includes providing distance markers along the shaft/handle to enable the operator to gage distance when retracting the treatment device. Yet another optional enhancement includes providing an alternative actuator that combines control of elongated shaft rotation relative to the housing assembly with control of elongated shaft distal region deflection. Still another optional enhancement includes providing an actuator on the handle assembly for controlling the delivery of energy, taking measurements, or activating a sensor. Another optional enhancement includes providing an audio or visual signal that indicates sensor feedback or amount of deflection or rotation.

IV. Use of the System

A. Intravascular Delivery, Deflection and Placement of the Treatment Device Any one of the embodiments of the treatment devices 12 described herein can be delivered over a guide wire using conventional over-the-wire techniques. When delivered in this manner (not shown), the elongated shaft 16 includes a passage or lumen accommodating passage of a guide wire.

Alternatively, any one of the treatment devices 12 described herein can be deployed using a conventional guide catheter or pre-curved renal guide catheter (not shown).

When using a guide catheter, the femoral artery is exposed and cannulated at the base of the femoral triangle, using conventional techniques. In one exemplary approach, a guide wire (not shown) is inserted through the access site and passed using image guidance through the femoral artery, into the iliac artery and aorta, and into either the left or right renal artery. A guide catheter can be passed over the guide wire into the accessed renal artery. The guide wire is then removed. Alternatively, a renal guide catheter, which is specifically shaped and configured to access a renal artery, can be used to avoid using a guide wire. Still alternatively, the treatment device can be routed from the femoral artery to the renal artery using angiographic guidance and without the need of a guide catheter.

When a guide catheter is used, at least three delivery approaches can be implemented. In one exemplary approach, one or more of the aforementioned delivery techniques can be used to position a guide catheter within the renal artery just distal to the entrance of the renal artery. The treatment device is then routed via the guide catheter into the renal artery. Once the treatment device is properly positioned within the renal artery, the guide catheter is retracted from the renal artery into the abdominal aorta. In this approach, the guide catheter should be sized and configured to accommodate passage of the treatment device. For example, a 6 French guide catheter can be used.

In a second exemplary approach, a first guide catheter is placed at the entrance of the renal artery (with or without a guide wire). A second guide catheter is passed via the first guide catheter (with or without the assistance of a guide wire) into the renal artery. The treatment device is then routed via the second guide catheter into the renal artery. Once the treatment device is properly positioned within the renal artery the second guide catheter is retracted, leaving the first guide catheter at the entrance to the renal artery. In this approach the first and second guide catheters should be sized and configured to accommodate passage of the second guide catheter within the first guide catheter (i.e., the inner diameter of the first guide catheter should be greater than the outer diameter of the second guide catheter). For example, the first guide catheter could be 8 French in size and the second guide catheter could be 5 French in size.

In a third exemplary approach, a renal guide catheter is positioned within the abdominal aorta, just proximal to the entrance of the renal artery. The treatment device 12 as described herein is passed through the guide catheter and into the accessed renal artery. The elongated shaft 16 makes atraumatic passage through the guide catheter, in response to forces applied to force transmitting section 30 of the shaft through handle assembly 200. The proximal flexure zone 32 accommodates significant flexure at the junction of the left/right renal arteries and aorta to gain entry into the respective left or right renal artery through the guide catheter.

Figure 9A:
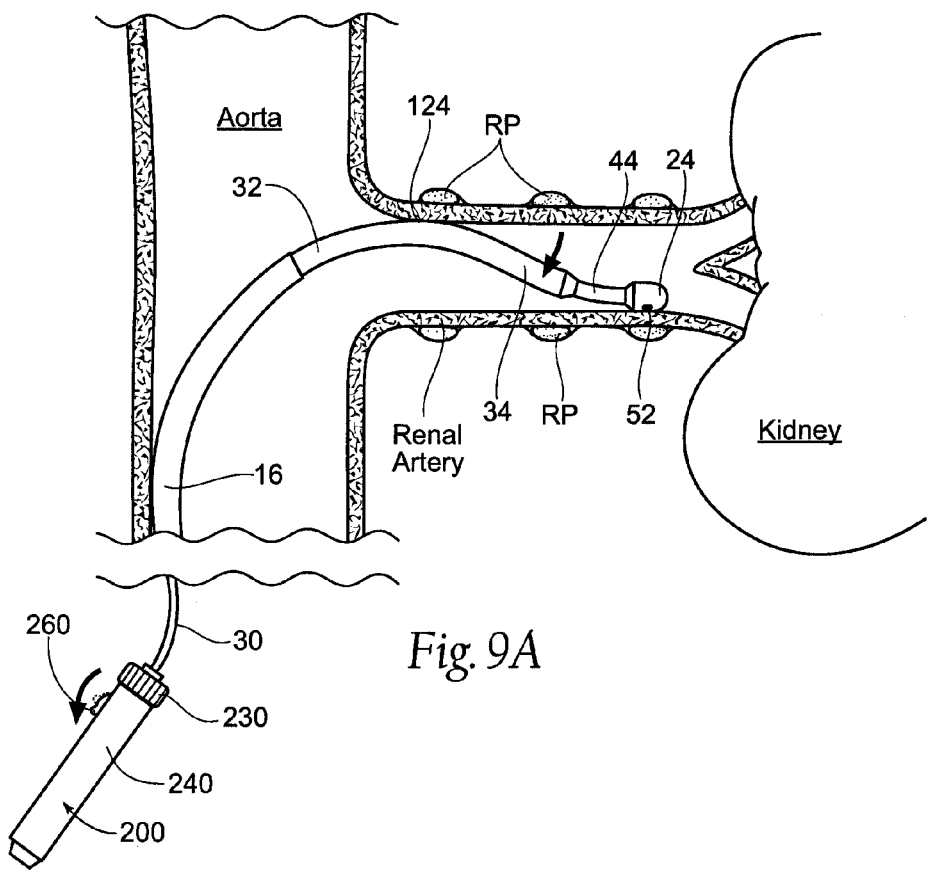

As seen in FIG. 9A, the intermediate flexure zone 34 on the distal end portion of the elongated shaft 16 can be axially translated into the respective renal artery, remotely deflected and/or rotated in a controlled fashion within the respective renal artery to attain proximity to and a desired alignment with an interior wall of the respective renal artery. The distal flexure zone 44 bends to place the thermal heating element 24 into contact with tissue on the interior wall of the renal artery.

Figure 9B:
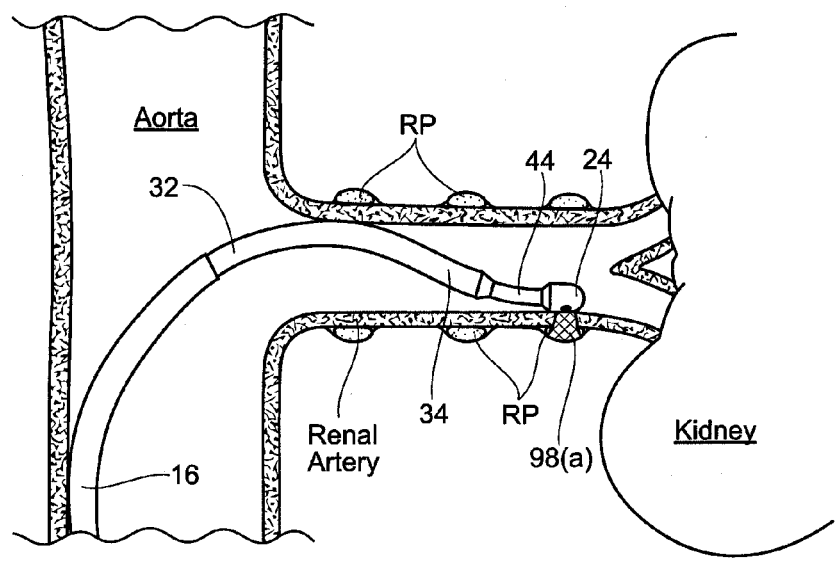

As seen in FIG. 9B, the complex, multi-bend structure formed by the proximal, intermediate and distal zones 32, 34, and 44 of the distal end region 20 of the elongated shaft 16 creates a consistent and reliable active surface area of contact between the thermal heating element 24 and tissue within the respective renal artery. Thermal energy can now be applied through the thermal heating element 24 to induce one or more thermal heating effects on localized regions of tissue along the respective renal artery.

B. Facilitating Contact with the Vessel Wall

As previously described, the actuation of the control wire 40 to deflect the intermediate flexure zone 34 helps position the thermal heating element 24 in contact with the vessel wall. This is particularly useful when the distal end region 20 of the treatment device 12 is delivered into the renal artery. Due to the curve and placement of the (optional) renal guide catheter and orientation of the treatment device 12, the distal end region 20 of the treatment device may be oriented up against the superior region of the vessel wall when first delivered into the renal artery. Once the distal end region is positioned at the most distal portion of the main renal artery, the operator may deflect the intermediate flexure zone 34 via the actuator 260, which is coupled to carrier 280 and control wire 40, to position the thermal heating element 24 into contact with the vessel wall at a more inferior location, as shown in FIG. 9A. This deflection of the intermediate flexure zone 34 establishes wall contact and provides, via the distal flexure zone 44, a stabilizing force between the thermal heating element 24 and vessel wall to position the thermal heating element in contact with the vessel wall. The operator can then initiate treatment at this generally inferior (bottom) location or, as shown in FIG. 9C, rotate the treatment device 12 via rotator 230 for an alternate treatment location.

The active deflection of intermediate flexure zone 34 is facilitated not only by operation of actuator 260, but also by contact between a proximal region of the intermediate flexure zone 34 and a superior region of the renal artery. As shown in FIG. 9A, this contact region 124 generally occurs at the apex of the bend of the intermediate flexure zone 34. This contact region 124 is in radial opposition to the contact between the thermal heating element 24 and vessel wall following deflection of the intermediate flexure zone 34. The stabilizing force provided by the intermediate flexure zone 34 to the thermal heating element 24 is also facilitated by the opposing force at contact region 124. Even when the operator rotates the treatment device to circumferentially reposition the thermal heating element, as shown in FIG. 9C, this opposition contact will be maintained, but at a different circumferential position. FIG. 9D shows the circumferential rotation of the thermal heating element 24 from a first treatment location corresponding to lesion 98(*a*) to a second treatment location corresponding to lesion 98(*b*) and the circumferential translation of the intermediate flexure zone 34 to a new contact region 124. It should be noted, however, that while having such opposition contact at contact region 124 facilitates wall contact and the stabilizing force, it is not generally required to achieve contact between the thermal heating element 24 and the vessel wall.

In certain embodiments, it may also be beneficial to equip the catheter apparatus with a second thermal heating element (not shown) at or in the vicinity of the intermediate flexure zone. Placement of the second thermal heating element on or proximate to the intermediate flexure zone may enable the creation of a thermally affected tissue region at or around contact region 124 (i.e., the portion of the vessel wall that is in contact with the intermediate flexure zone). Activation of the first thermal element and the second thermal element would allow the operator to create two treatment zones that are circumferentially and longitudinally offset during a single placement of the catheter apparatus.

C. Creation of Thermally Affected Tissue Regions

As previously described, the thermal heating element 24 can be positioned by bending along the proximal flexure zone 32 at a first desired axial location within the respective renal artery. As FIG. 9A shows, the thermal heating element 24 can be radially positioned by deflection of intermediate flexure zone 34 toward the vessel wall. As FIG. 9A also shows, the thermal heating element 24 can be placed into a condition of optimal surface area contact with the vessel wall by further deflection of the distal flexure zone 44.

Once the thermal heating element 24 is positioned in the desired location by a combination of deflection of the intermediate flexure zone 34, deflection of the distal flexure zone 44 and rotation of the catheter, the first focal treatment can be administered. By applying energy through the thermal heating element 24, a first thermally affected tissue region 98(*a*) can be formed, as FIG. 9B shows. In the illustrated embodiment, the thermally affected region 98(*a*) takes the form of a lesion on the vessel wall of the respective renal artery.

After forming the first thermally affected tissue region 98(*a*), the catheter needs to be repositioned for another thermal treatment. It is desirable to create multiple focal lesions that are circumferentially spaced along the longitudinal axis of the renal artery. To achieve this result, the catheter is retracted and, optionally, rotated to position the thermal heating element proximally along the longitudinal axis of the blood vessel. Rotation of the elongated shaft 16 from outside the access site (see FIG. 9C), e.g., via rotation of the rotator 230 relative to the housing assembly 240, serves to circumferentially reposition the thermal heating element 24 about the renal artery.

Once the thermal heating element 24 is positioned at a second axial and circumferential location within the renal artery (e.g., 98(*b*)) spaced from the first-described axial position, as shown in FIGS. 9C and 9D, another focal treatment can be administered. By repeating the manipulative steps just described, the caregiver can create several thermally affected tissue regions on the vessel wall that are axially and circumferentially spaced apart, with the first thermally affected tissue region 98(*a*) being the most distal and the subsequent thermally affected tissue regions being more proximal (or vice versa). Several circumferentially and axially spaced-apart treatments can provide substantially circumferential coverage and, accordingly, cause a neuromodulatory affect to the renal plexus. Clinical investigation indicates that each lesion will cover approximately 20-30 percent of the circumferential area surrounding the renal artery. In other embodiments, the circumferential coverage of each lesion can be as much as 50 percent.

V. Additional Embodiments

A. Maintenance of Longitudinal Position During Deflection

As described above, it may be desirable for the clinical treatment provider to use the treatment device to create multiple thermally affected treatment regions along the longitudinal axis of the blood vessel. Typically, the most distal treatment region would be created first and the treatment device would be retracted longitudinally to position the thermal element of the treatment device in subsequent proximal locations along the longitudinal axis of the blood vessel. In certain configurations it may be advantageous to separated sequential treatment regions by a specified distance (e.g., 5 mm). To achieve accurate and consistent separation between consecutive treatment regions, the treatment provider may decide to rely on the positioning of the thermal element from the previous treatment region as a reference point.

Figure 10A:
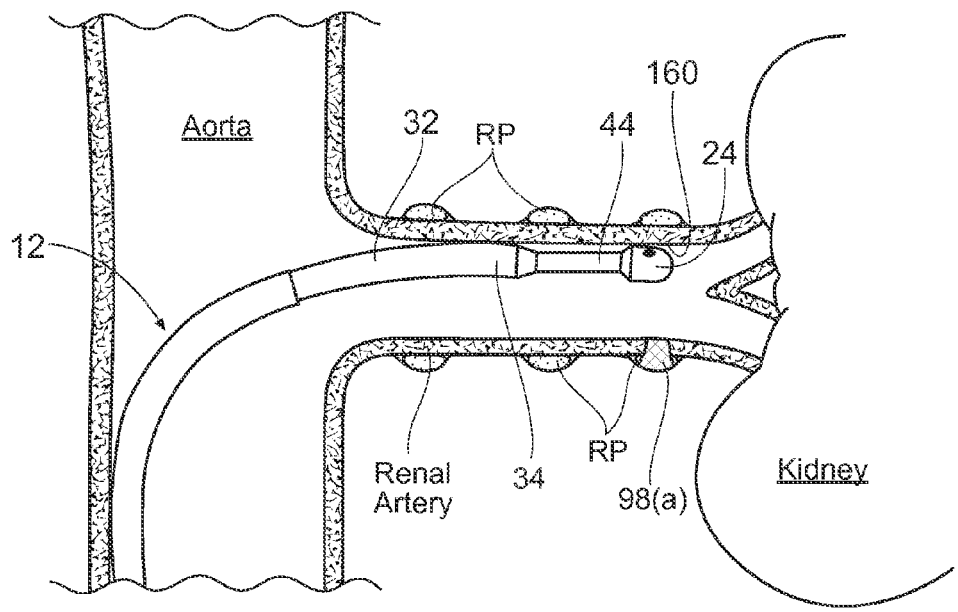
FIGS. 10A and 10B illustrate the radial and longitudinal translation of the thermal element upon deflection of the intermediate flexure zone of the treatment device.
Figure 10B:
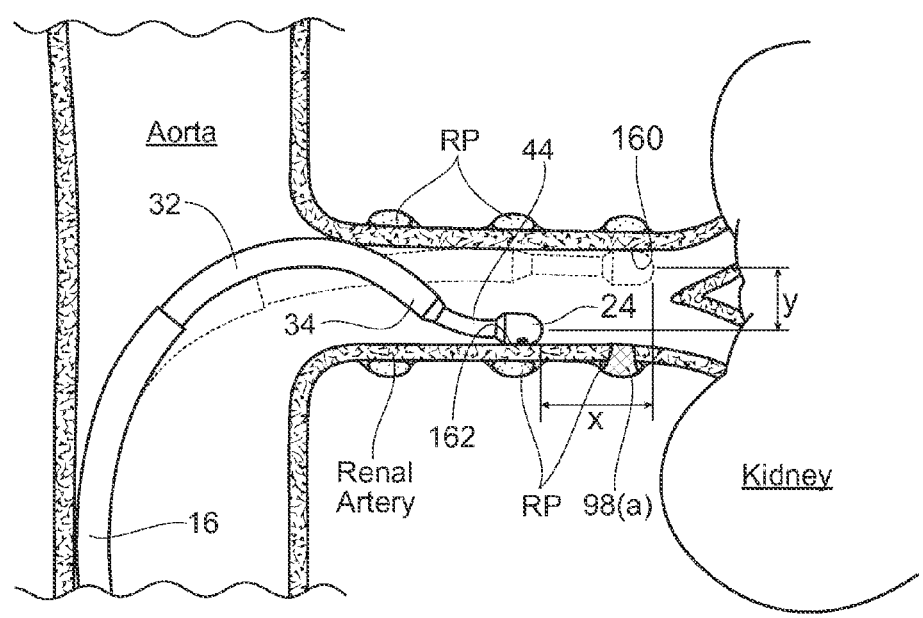

As shown in FIG. 10A, the thermal element 24 is initially positioned within the blood vessel at distal location 160 when the distal end region of the treatment device is in a substantially straight configuration. Upon operation of the actuator 260, the intermediate flexure zone 34 may be deflected to translate the thermal element, and position the thermal element in contact with the vessel wall at location 162. As shown in FIG. 10B, translation of the thermal element has two components: radially away from the axis of the distal end region (Y) and proximally along the longitudinal axis of the blood vessel (X). If the distal end region of the treatment device is returned to a substantially straight configuration (e.g., via returning actuator 260 to its original position) following creation of a treatment region and, accordingly the thermal element is returned to location 160, the thermal element is now longitudinally distal to the treatment region by a distance of X (i.e., the longitudinal separation between location 160 and 162 is X). This distance X might compromise accurate positioning of the thermal element for a subsequent proximal treatment since the treatment provider might use location 160 as a reference point.

Figure 11:
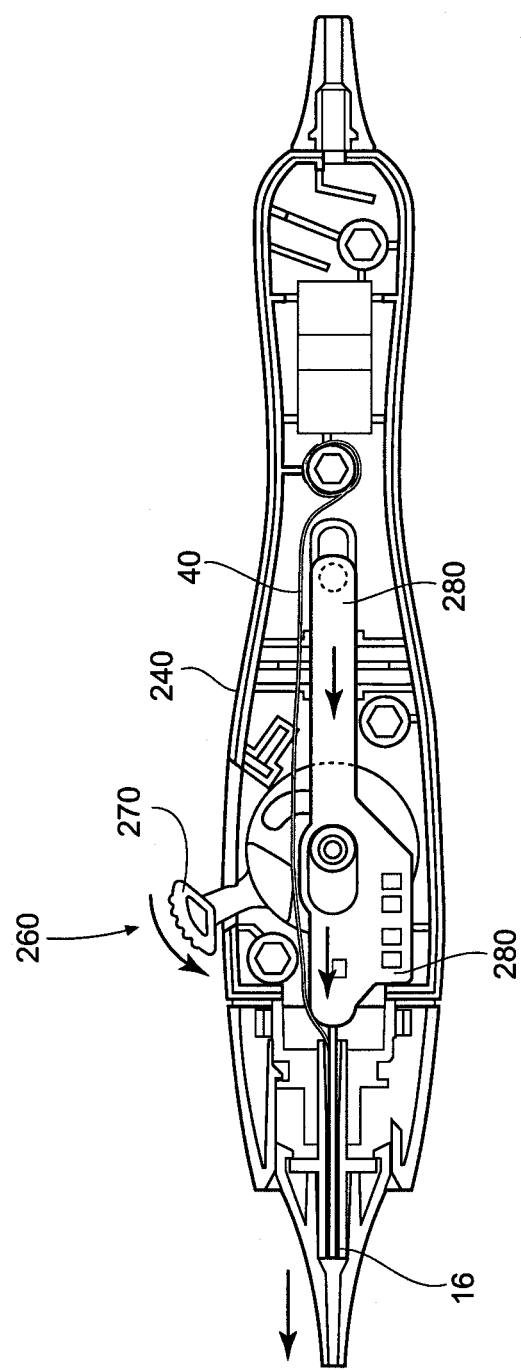
FIG. 11 illustrates an alternative embodiment of the handle assembly.

This potential positioning concern described above can be addressed by reconfiguring the design of the handle and, particularly, the housing assembly 240, elongate shaft 16, control wire 40 and carrier 280. In the previously described embodiments, carrier 280 is proximally retracted upon operation of actuator 260 to apply tension to and axially retract control wire 40 relative to the elongated shaft 16. This tension will cause intermediate flexure zone 34 to deflect and/or buckle, thereby facilitating translation of thermal element 24. In the alternative embodiment illustrated in FIG. 11, handle 200 is configured such that control wire 40 cannot move axially relative to the housing assembly 240. More specifically, elongated shaft 16 is coupled to carrier 280 such that axial movement of carrier 280 relative to housing assembly 240 causes axial movement of elongated shaft 16 relative to control wire 40. As shown in FIG. 11, actuator 260 begins in a proximal position such that distal movement of actuator button 270 causes distal axial movement of carrier 280 and elongated shaft 16. Distal movement of elongated shaft 16 relative to control wire 40 will create tension in the distal end region of the treatment device, thereby causing deflection and/or buckling of the intermediate flexure zone. Since control wire 40 cannot move axially relative to the housing assembly 240, deflection of the intermediate flexure zone 34 in this configuration occurs without significant longitudinal translation of the thermal element.

B. Combined Actuator and Rotator

Although the above described embodiment might facilitate accurate positioning and separation of the thermal element for consecutive treatment regions, coupling the elongated shaft to the carrier of the actuator assembly may compromise independent rotation of the shaft relative to the handle. One potential enhancement to address this concern would be to incorporate a rotational coupling (e.g., slip ring connector) into the handle assembly to allow for rotation of the elongated shaft independent of the housing assembly.

In an alternate embodiment, the housing assembly may be configured with a distal region and a proximal region wherein the distal region comprises a rotator to facilitate rotation of the distal region independent of the proximal region. In this embodiment, the distal region also includes the actuator assembly, which comprises the actuator and carrier, wherein the carrier is fixedly coupled to the carrier. In this configuration, the distal region of the housing assembly may rotate the elongated shaft independent of the proximal region of the housing assembly.

CONCLUSION

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. As another example, the system 10 may have a different configuration and/or include different features, such as multi-thermal heating element devices, e.g., multi-electrode baskets or other balloon expandable devices that may be implemented to intravascularly deliver neuromodulatory treatment with or without contacting the vessel wall. The various embodiments described herein can also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the invention. Accordingly, the invention is not limited except as by the appended claims.

We claim:

1. A handle assembly, comprising:
    a housing;
    a rotator coupled to a proximal region of an elongated flexible shaft extending rotatably along an axis and having a deflectable distal region configured for intravascular delivery to a blood vessel of a human patient, wherein the rotator is configured to rotate the entire elongated flexible shaft through the proximal region without rotating the housing;
    a rotational limiting element configured to prevent rotation of the elongated flexible shaft and the rotator beyond a predetermined number of rotations; and
    an actuator coupled to a carrier, which in turn is coupled to a control wire extending within a lumen of the elongated flexible shaft to the deflectable distal region such that the actuator is operatively connected to the deflectable distal region of the elongated flexible shaft;
    wherein the actuator is configured to rotate relative to the housing, and wherein the carrier is coupled to the actuator in a manner that converts rotation of the actuator into translation of the carrier, and
    the actuator is further configured to proximally translate the carrier relative to the housing to apply tension to the control wire and thereby deflect the deflectable distal region of the elongated flexible shaft.

2. The handle assembly of claim 1 wherein a coupling of the actuator and the carrier comprises a cam configured to converts rotation of the actuator into translation of the carrier.

3. The handle assembly of claim 1 wherein the actuator is coupled to the carrier within the housing.

4. The handle assembly of claim 1, further comprising a connector coupling a thermal element at the deflectable distal region of the elongated flexible shaft to a thermal energy source for delivery of thermal energy to the thermal element.

5. The handle assembly of claim 1, further comprising a connector coupled to at least one sensor at the deflectable distal region of the elongated flexible shaft for receipt of a signal transmitted by the sensor.

6. The handle assembly of claim 1 wherein the rotational limiting element is configured to limit rotation of the elongated flexible shaft to a predetermined number of rotations in the range of about 1 to 3 rotations.

7. The handle assembly of claim 1 wherein the rotational limiting element is configured to prevent rotation of the elongated flexible shaft beyond about 2 rotations.

8. The handle assembly of claim 1 wherein the rotational limiting element comprises a geometric constraint to continued rotation of the rotator that prevents rotation of the elongated flexible shaft beyond the predetermined number of rotations.

9. The handle assembly of claim 8 wherein the geometric constraint comprises an abutment of the rotator and the housing.

10. The handle assembly of claim 9 wherein the abutment further comprises at least one rotation limiter ring positioned between the rotator and the housing and configured to extend rotation of the elongated flexible shaft to the predetermined number of rotations.

11. The handle assembly of claim 9 wherein the abutment further comprises a ball positioned within a fixed length helical channel formed between the rotator and housing.

12. The handle assembly of claim 1 wherein the housing further comprises a conforming surface that substantially conforms to a surface on which the handle assembly is placed during use.

13. The handle assembly of claim 1 wherein the elongated flexible shaft further comprises an intravascular treatment device configured for delivery to a renal artery of the patient.

\* \* \* \* \*